US009289967B2

(12) United States Patent
Ordway et al.

(10) Patent No.: US 9,289,967 B2
(45) Date of Patent: *Mar. 22, 2016

(54) METHODS FOR BONDING SUBSTRATES

(71) Applicant: The Procter & Gamble Company, Cincinnati, OH (US)

(72) Inventors: David Carlton Ordway, Oxford, OH (US); Jillian Marie Franke, Madeira, OH (US); Gene Xiaoqing Huang, Mason, OH (US); Uwe Schneider, Cincinnati, OH (US); Michael Devin Long, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 130 days.

This patent is subject to a terminal disclaimer.

(21) Appl. No.: 14/038,812

(22) Filed: Sep. 27, 2013

(65) Prior Publication Data

US 2014/0110053 A1    Apr. 24, 2014

Related U.S. Application Data

(60) Provisional application No. 61/717,268, filed on Oct. 23, 2012.

(51) Int. Cl.
| | | |
|---|---|---|
| *A61F 13/15* | (2006.01) | |
| *B32B 33/00* | (2006.01) | |
| *A61F 13/496* | (2006.01) | |

(52) U.S. Cl.
CPC ........... *B32B 33/00* (2013.01); *A61F 13/15739* (2013.01); *A61F 13/4963* (2013.01)

(58) Field of Classification Search
None
See application file for complete search history.

(56) References Cited

U.S. PATENT DOCUMENTS

| | | |
|---|---|---|
| 3,860,003 A | 1/1975 | Buell |
| 4,610,678 A | 9/1986 | Weisman et al. |
| 4,673,402 A | 6/1987 | Weisman et al. |
| 4,695,278 A | 9/1987 | Lawson |
| 4,704,115 A | 11/1987 | Buell |
| 4,795,454 A | 1/1989 | Dragoo |
| 4,834,735 A | 5/1989 | Alemany et al. |
| 4,888,231 A | 12/1989 | Angstadt |
| 4,909,803 A | 3/1990 | Aziz et al. |

(Continued)

FOREIGN PATENT DOCUMENTS

WO    WO 2011/156299 A1    12/2011

OTHER PUBLICATIONS

PCT International Search Report (PCT/US2013/065867) dated Dec. 18, 2013, 10 pages.

*Primary Examiner* — Barbara J Musser
(74) *Attorney, Agent, or Firm* — Sarah M. DeCristofaro; Abbey A. Lopez

(57) ABSTRACT

A method includes rotating a drum about an axis and rotating an anvil roll about an axis adjacent to the drum so as to form a nip there between. The drum includes a fluid nozzle and a press member, the press member having an outer surface. The anvil roll includes a compliant outer circumferential surface. First and second substrates are advanced in a machine direction onto the drum. The fluid nozzle moves radially outward and a jet of heated fluid is directed onto the substrates. The fluid nozzle retracts radially inward and the press member is shifted radially outward. The substrates are advanced through the nip and compressed between the press member and the anvil roll such that the press member deforms the compliant outer circumferential surface of the anvil roll.

20 Claims, 22 Drawing Sheets

(56) References Cited

U.S. PATENT DOCUMENTS

| | | |
|---|---|---|
| 5,562,646 A | 10/1996 | Goldman et al. |
| 5,599,335 A | 2/1997 | Goldman et al. |
| 5,628,097 A | 5/1997 | Benson et al. |
| 5,669,894 A | 9/1997 | Goldman et al. |
| 5,779,831 A | 7/1998 | Schmitz |
| 5,916,661 A | 6/1999 | Benson et al. |
| 6,107,539 A | 8/2000 | Palumbo et al. |
| 6,248,195 B1 | 6/2001 | Schmitz |
| 6,545,197 B1 | 4/2003 | Muller et al. |
| 6,790,798 B1 | 9/2004 | Suzuki et al. |
| 7,569,039 B2 | 8/2009 | Matsuda et al. |
| 7,587,966 B2 | 9/2009 | Nakakado et al. |
| 2004/0097895 A1 | 5/2004 | Busam et al. |
| 2004/0107764 A1 | 6/2004 | Yan |
| 2004/0158212 A1 | 8/2004 | Ponomarenko et al. |
| 2010/0233428 A1* | 9/2010 | Stone et al. .............. 428/133 |
| 2011/0151171 A1 | 6/2011 | Biegler et al. |
| 2012/0021186 A1 | 1/2012 | Schneider |
| 2012/0061015 A1 | 3/2012 | LaVon et al. |
| 2012/0061016 A1 | 3/2012 | LaVon et al. |
| 2013/0213547 A1 | 8/2013 | Schneider et al. |
| 2013/0218116 A1 | 8/2013 | Schneider et al. |

\* cited by examiner

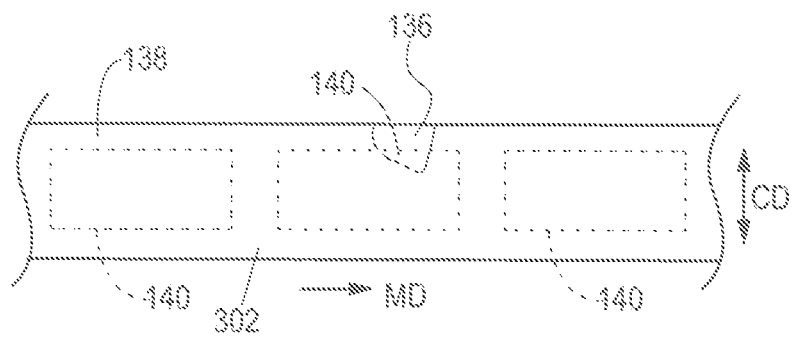
Fig. 5A
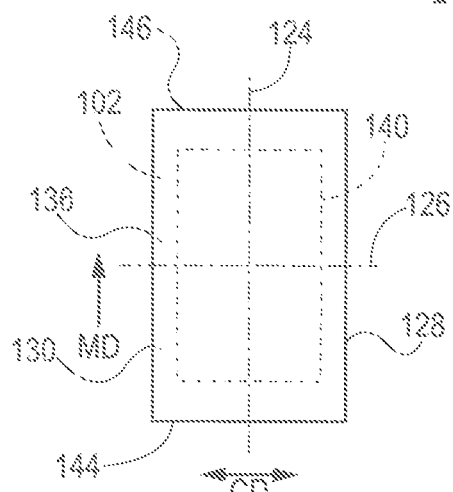
Fig. 5B1
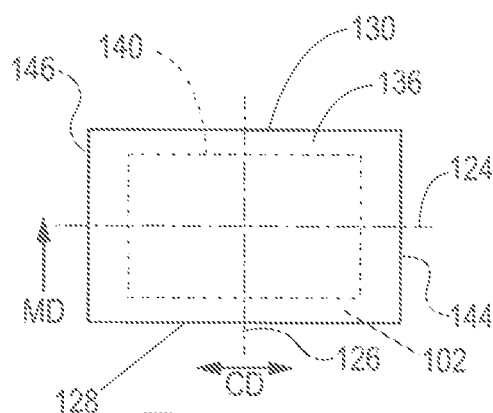
Fig. 5B2
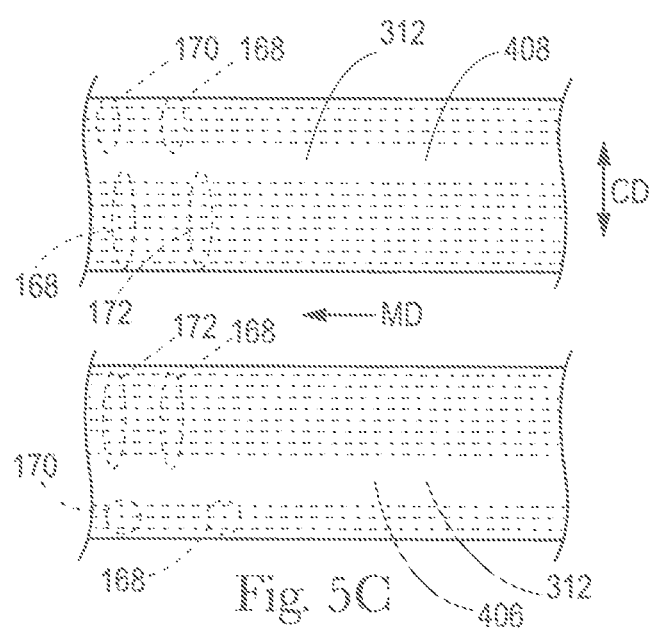
Fig. 5C

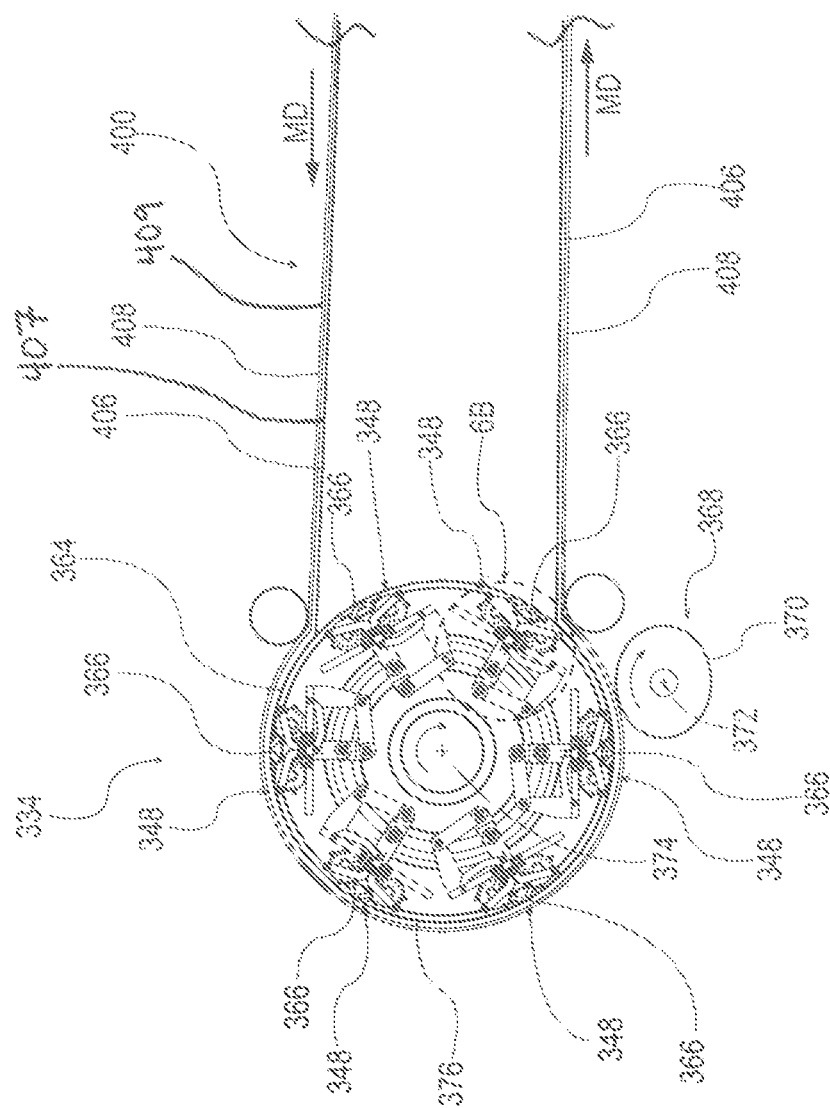

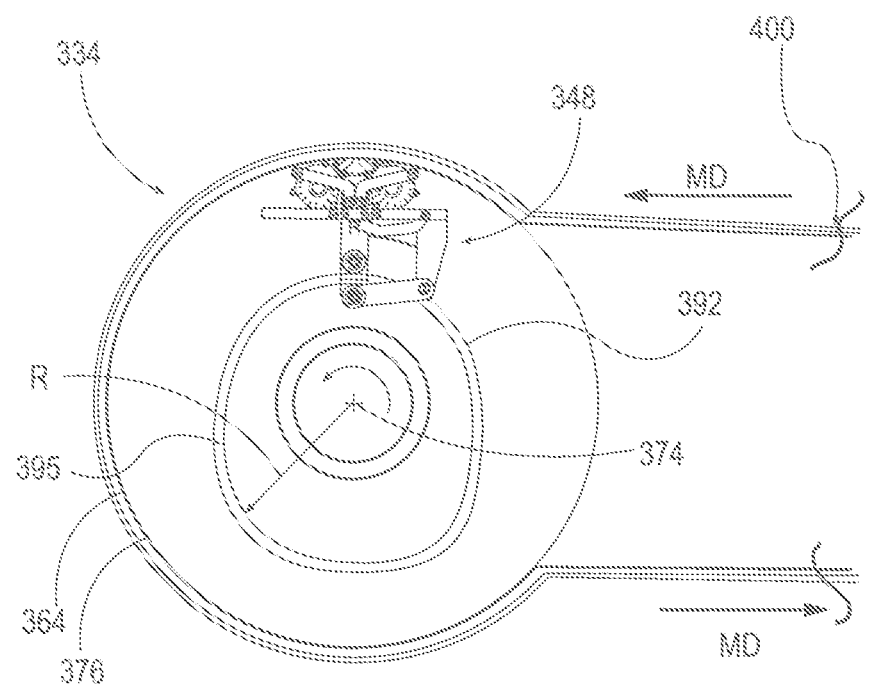
Fig. 6A1

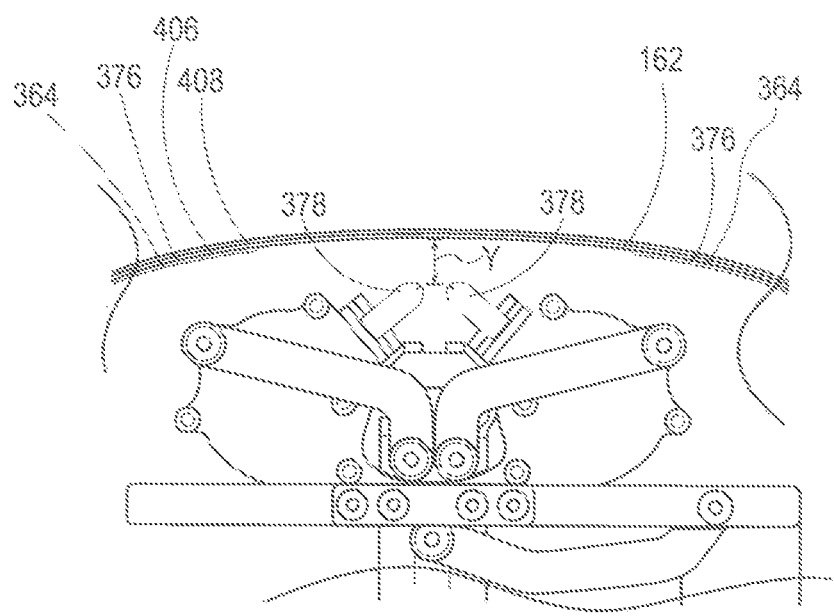
Fig. 6B1

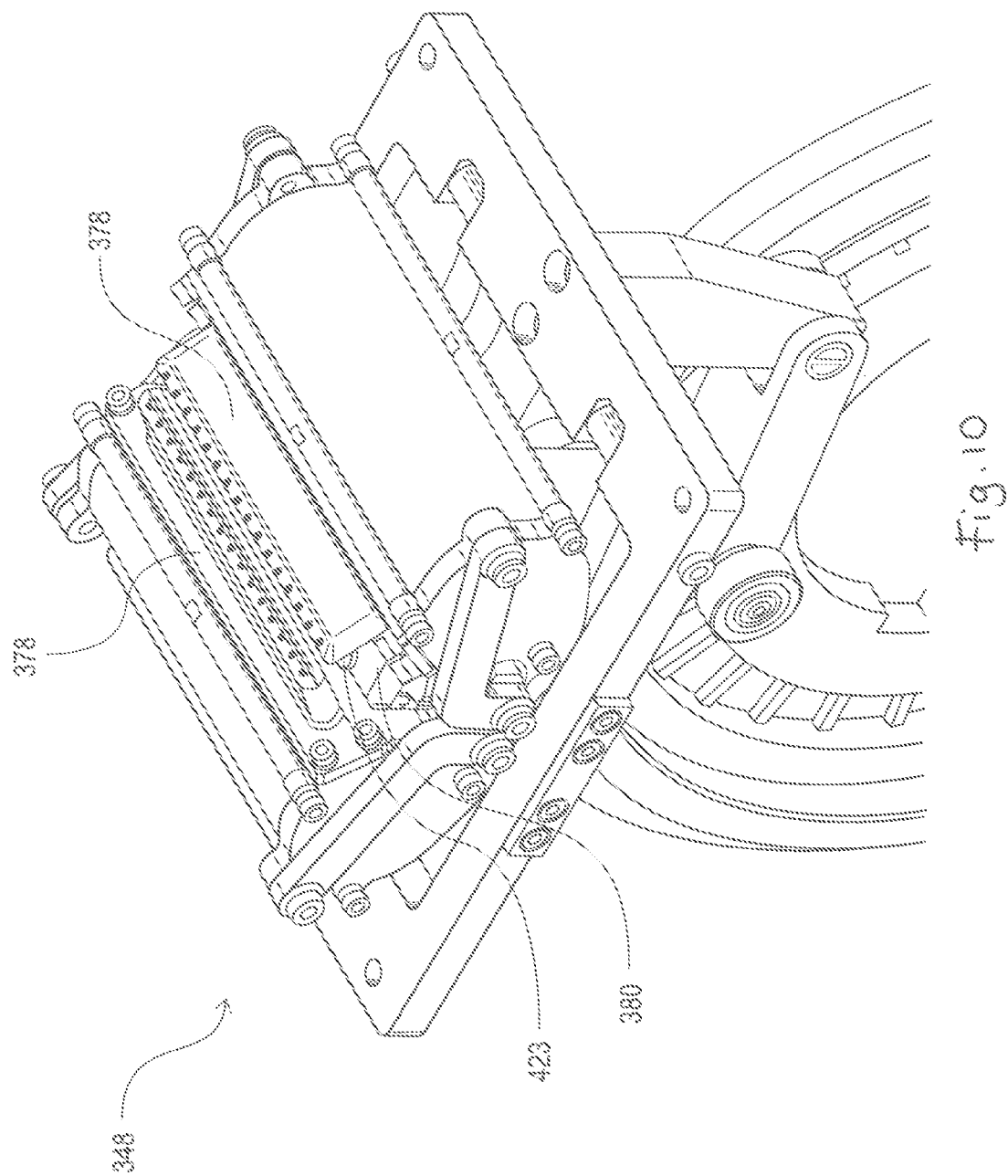

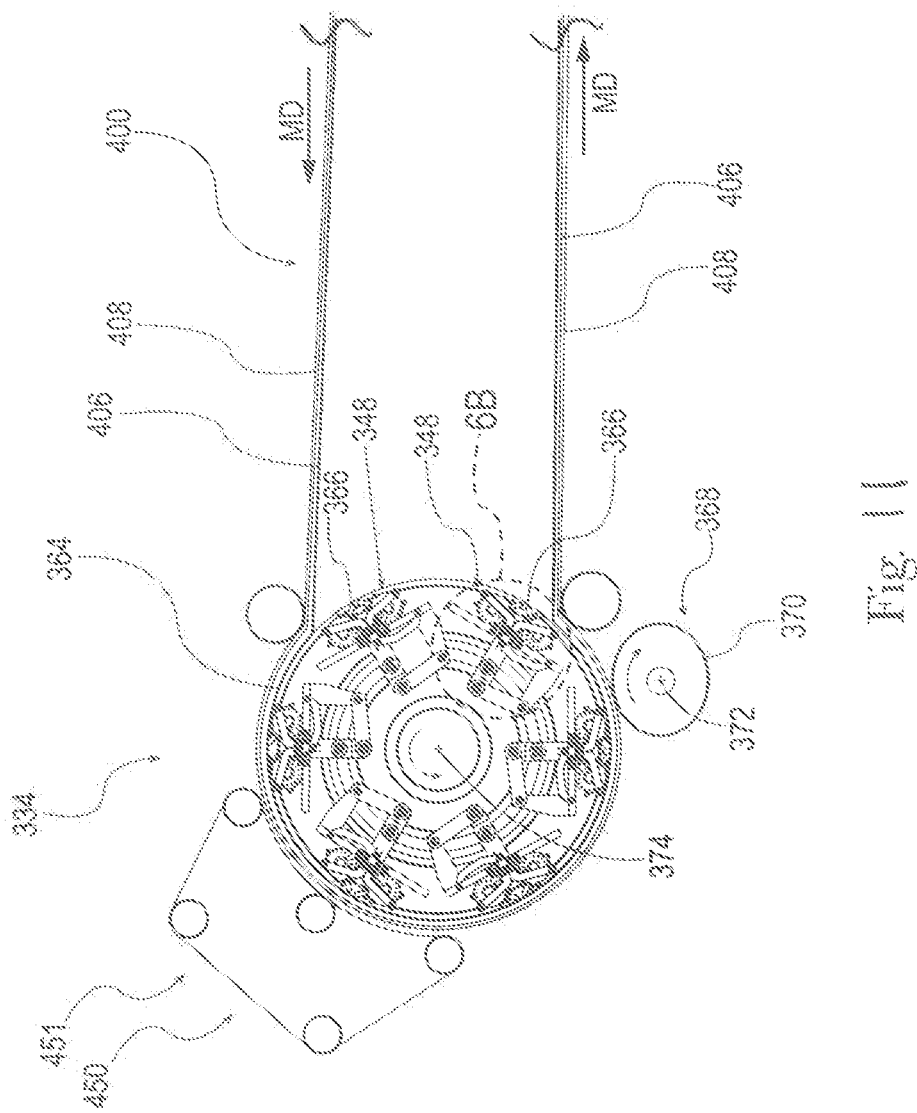

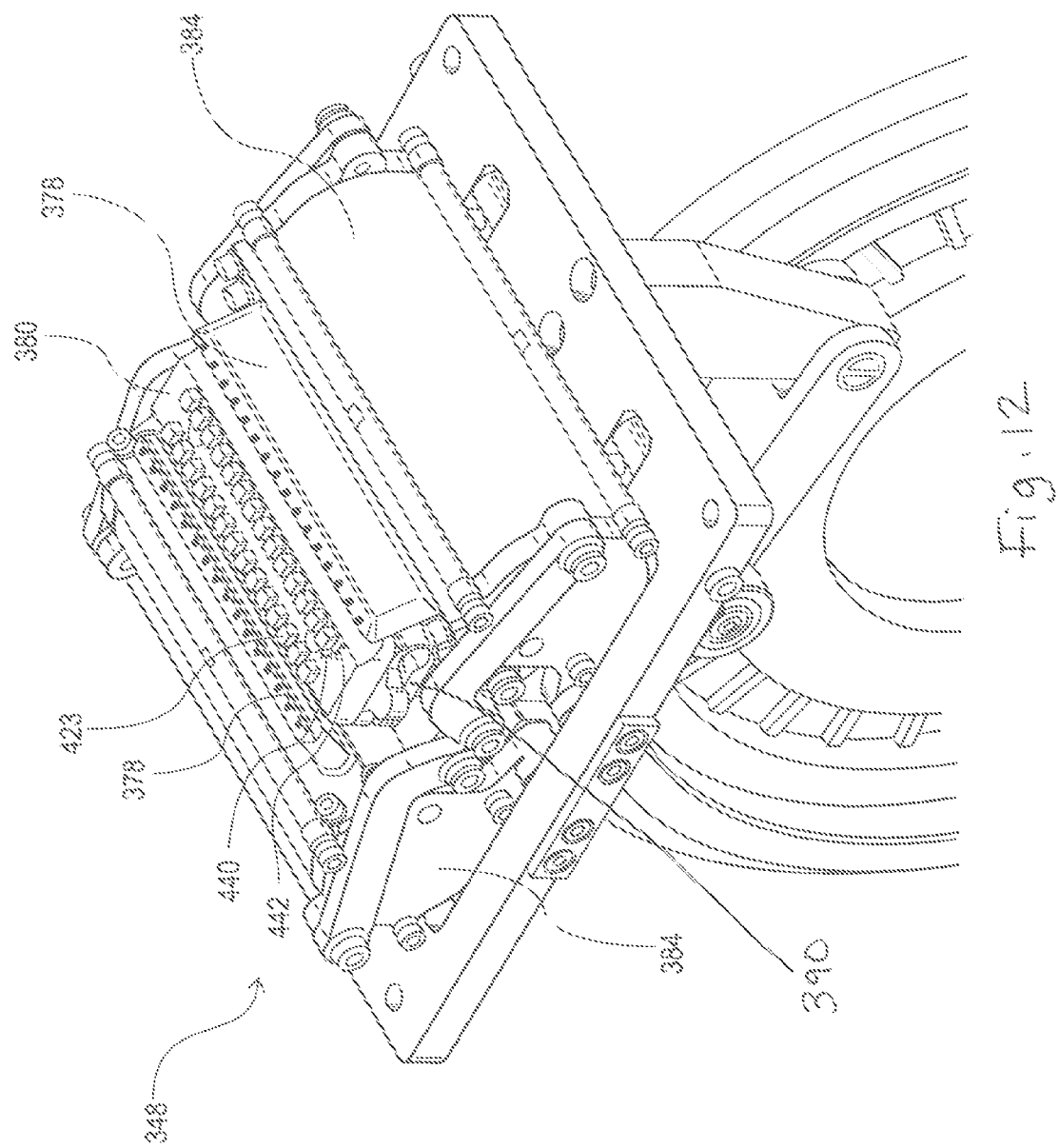

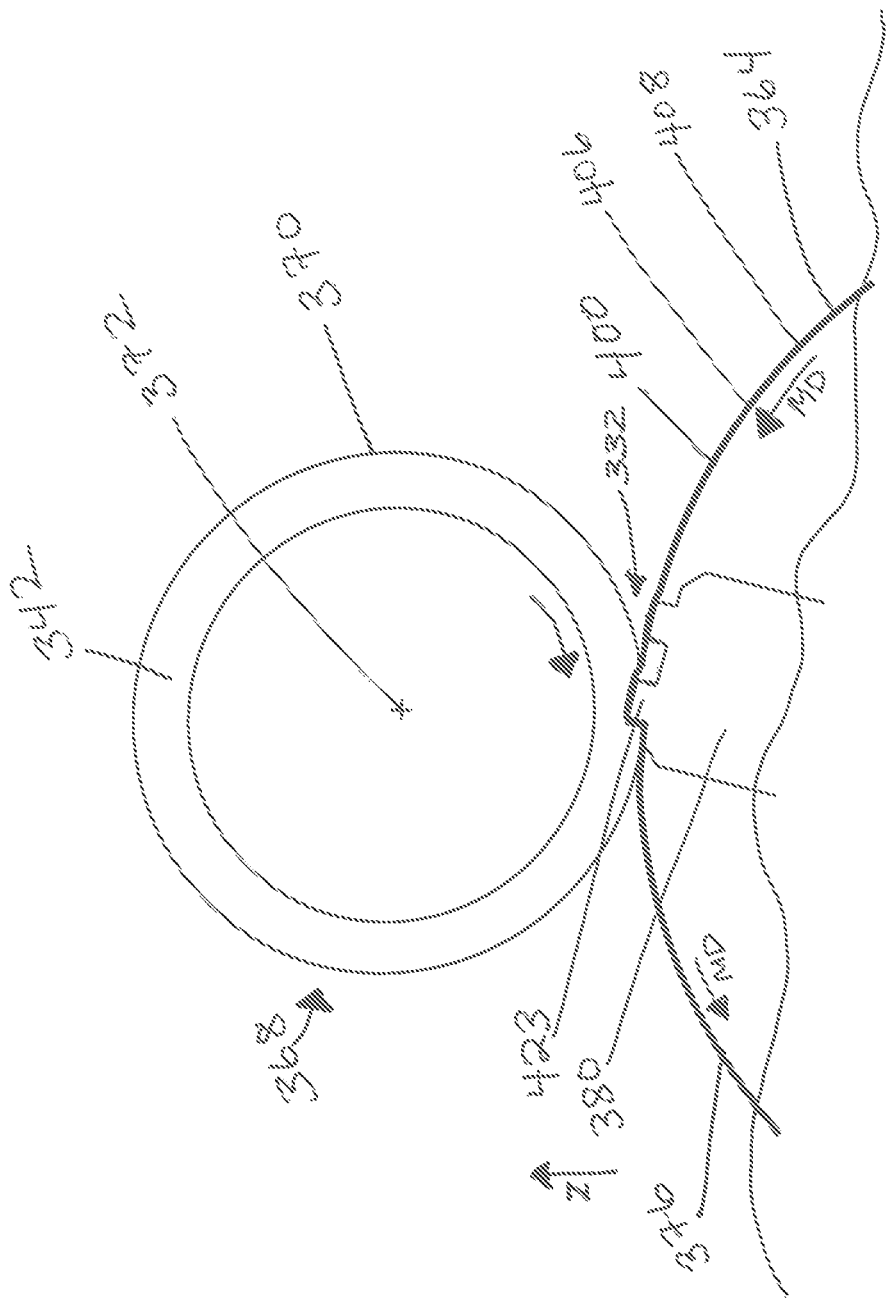

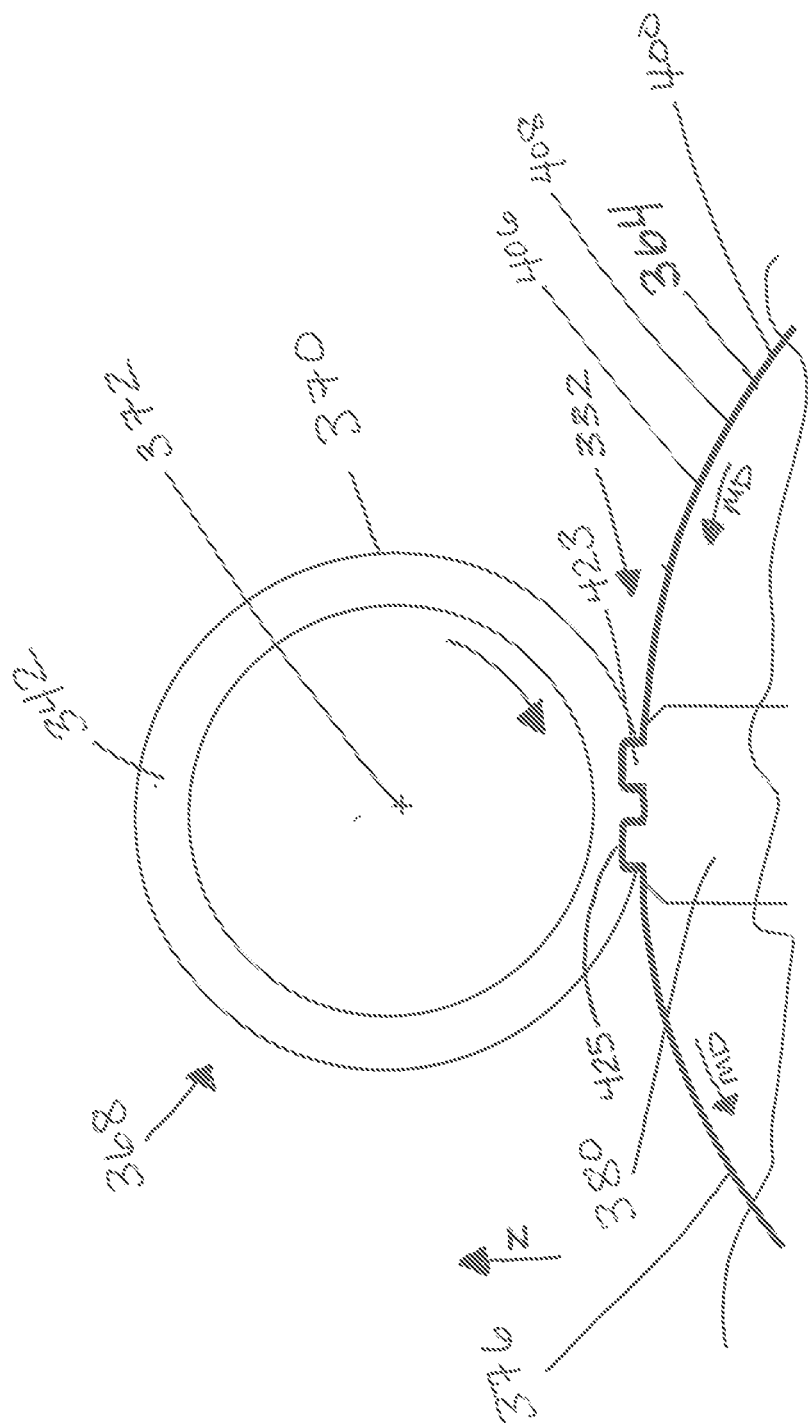

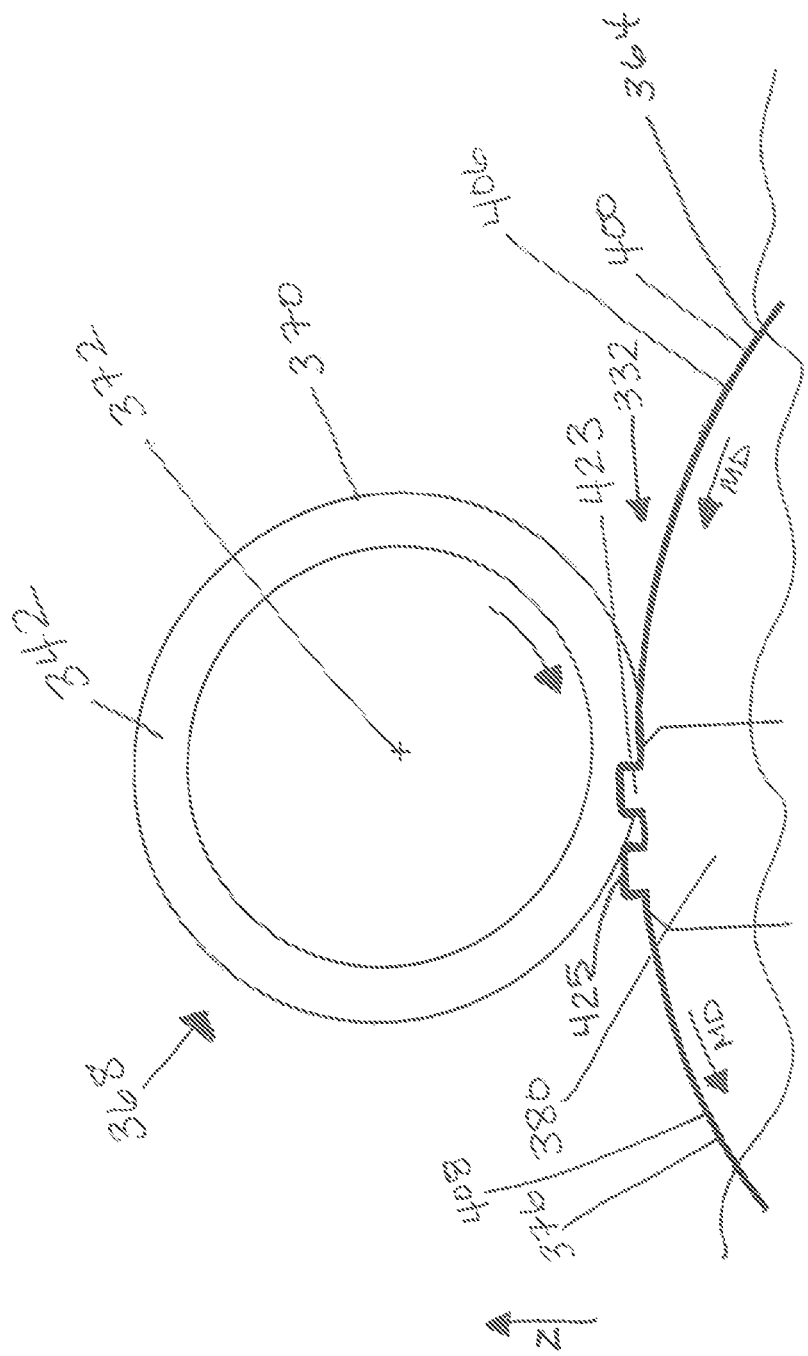

METHODS FOR BONDING SUBSTRATES

FIELD OF THE INVENTION

The present disclosure relates to methods for manufacturing absorbent articles, and more particularly, to apparatuses and methods for bonding substrates together during the manufacture of absorbent articles.

BACKGROUND OF THE INVENTION

Along an assembly line, various types of articles, such as diapers and other absorbent articles, may be assembled by adding components to and/or otherwise modifying an advancing, continuous web of material. In some processes, advancing webs of material are combined with other advancing webs of material. In other processes, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

In some converting configurations, discrete chassis spaced apart from each other are advanced in a machine direction and are arranged with a longitudinal axis parallel with the cross direction. Opposing waist regions of discrete chassis are then connected with continuous lengths of elastically extendable front and back belt webs advancing in the machine direction. While connected with the chassis, the front and back belt webs are maintained in a fully stretched condition along the machine direction, forming a continuous length of absorbent articles. The continuous length of absorbent articles may then be folded in a cross direction. During the folding process in some converting configurations, one of the front and back belt webs is folded into a facing relationship with the opposing belt. The front and back belts may then be bonded together to create the side seams on diapers.

Portions of the front and back belt may be partially melted and compressed together to create side seams. The seaming process may include advancing the front and back belts through a nip formed between a rotating anvil roll and a rotating compression tool. As the front and back belts advance through the nip, the compression tool may compress the front and back belts against the anvil roll. The anvil and the compression tool may be made of a rigid material. In some processes, the amount of time that the front and back belts are compressed may affect the strength and quality of the seam. In particular, increased compression time may increase the quality and strength of the seam. However, in a high speed manufacturing process utilizing a rigid anvil roll and a rigid compression tool, the anvil roll and the compression tool may be spaced apart so as to prevent interference between the anvil roll and the compression tool. As a result, the compression time may be nearly instantaneous as the front and back belts pass through the nip formed between the anvil roll and the compression tool.

In some processes, compressing the advancing substrates in a direction that is non-tangential to both the outer surface of the compression tool and the outer circumferential surface of the anvil roll may improve the seam quality and strength. However, in a process utilizing a rigid compression tool and a rigid anvil roll spaced apart so as to prevent interference, the substrate may be compressed in a direction that is tangential to both the outer surface of the anvil roll and of the compression tool.

Thus, it would be beneficial to provide an apparatus and a method for increasing the compression time for bonding substrates together to form a side seam in a high speed manufacturing process. In addition, it would be beneficial to provide a process and apparatus for compressing substrates in a direction that is non-tangential to the outer surface of the compression tool and the outer circumferential surface of the anvil.

SUMMARY OF THE INVENTION

Aspects of the present disclosure include a method, the method comprising the steps of: rotating a drum about an axis of rotation, the drum comprising a fluid nozzle and a press member, the press member having an outer surface; rotating an anvil roll about an axis of rotation adjacent to the drum, the anvil roll having a compliant outer circumferential surface, the anvil roll and the drum forming a nip there between; advancing a first substrate layer in a machine direction onto the drum, the first substrate layer having an inner surface and an outer surface, wherein the outer surface of the first substrate layer is adjacent the drum; advancing a second substrate layer in the machine direction, the second substrate layer having an inner surface and an outer surface, wherein the first substrate layer is between the second substrate layer and the drum, wherein the first and second substrate layers have a combined, uncompressed caliper; wrapping the first and second substrate layers around a portion of the drum; heating a fluid to a temperature sufficient to at least partially melt the first and second substrate layers; moving the fluid nozzle radially outward relative to the axis of rotation of the drum; directing a jet of the heated fluid onto the first and second substrate layers; partially melting the first and second substrate layers; retracting the fluid nozzle radially inward relative to the axis of rotation of the drum; shifting the press member radially outward relative to the axis of rotation of the drum; advancing the first and second substrate layers through the nip; and compressing the first and second substrate layers between the press member and the anvil roll and deforming the compliant outer circumferential surface of the anvil roll.

Aspects of the present disclosure include an apparatus for bonding first and second substrates together, wherein the first and second substrates having a combined, uncompressed caliper. The apparatus comprises a drum comprising an outer circumferential surface and a drum aperture in the outer circumferential surface, wherein the drum is adapted to rotate about an axis of rotation. The apparatus comprises a fluid nozzle moveably connected to the drum, located radially inward relative to the drum aperture, and adapted to direct fluid radially outward through the drum aperture. The apparatus comprises an anvil roll comprising an outer circumferential surface located adjacent the drum so as to define a nip between the anvil roll and the drum. The anvil roll is adapted to rotate about an axis of rotation and comprises a compliant sleeve that defines the outer circumferential surface of the anvil roll. The outer circumferential surface of the anvil roll is deformable toward the axis of rotation of the anvil roll. The apparatus comprises a press member moveably connected to the drum, located radially inward relative to the drum aperture, and adapted to extend through the drum aperture.

BRIEF DESCRIPTION OF THE DRAWINGS

FIG. 2A is a partially cut away plan view of the diaper pant shown in FIG. 1.

FIG. 2B is a partially cut away plan view of a second configuration of a diaper pant.

FIG. 5A is a view of a continuous length of chassis assemblies from FIG. 4 taken along line A-A.

FIG. 5B1 is a view of a discrete chassis from FIG. 4 taken along line B1-B1.

FIG. 5B2 is a view of a discrete chassis from FIG. 4 taken along line B2-B2.

FIG. 5C is a view of continuous lengths of advancing front and back side panel material from FIG. 4 taken along line C-C.

FIG. 6A is a schematic side view of a bonder apparatus adapted to seam pre-fastened pant diapers.

FIG. 6A1 is a detailed, schematic side view of the bonder apparatus of FIG. 6A.

FIG. 6B1 is a detailed elevation view of the seamer station of FIG. 6B.

FIG. 10 is a perspective view of a seaming station in a first configuration.

FIG. 11 is a schematic side view of a bonder apparatus adapted to seam pre-fastened diapers.

FIG. 12 is a perspective view of a seaming station in the second configuration.

FIG. 13 is a partial, side elevation view of a press member and an anvil roll.

FIG. 14 is a partial, side elevation view of a press member and an anvil roll.

FIG. 15 is a partial, side elevation view of a press member and an anvil roll.

DETAILED DESCRIPTION OF THE INVENTION

Figure 1:
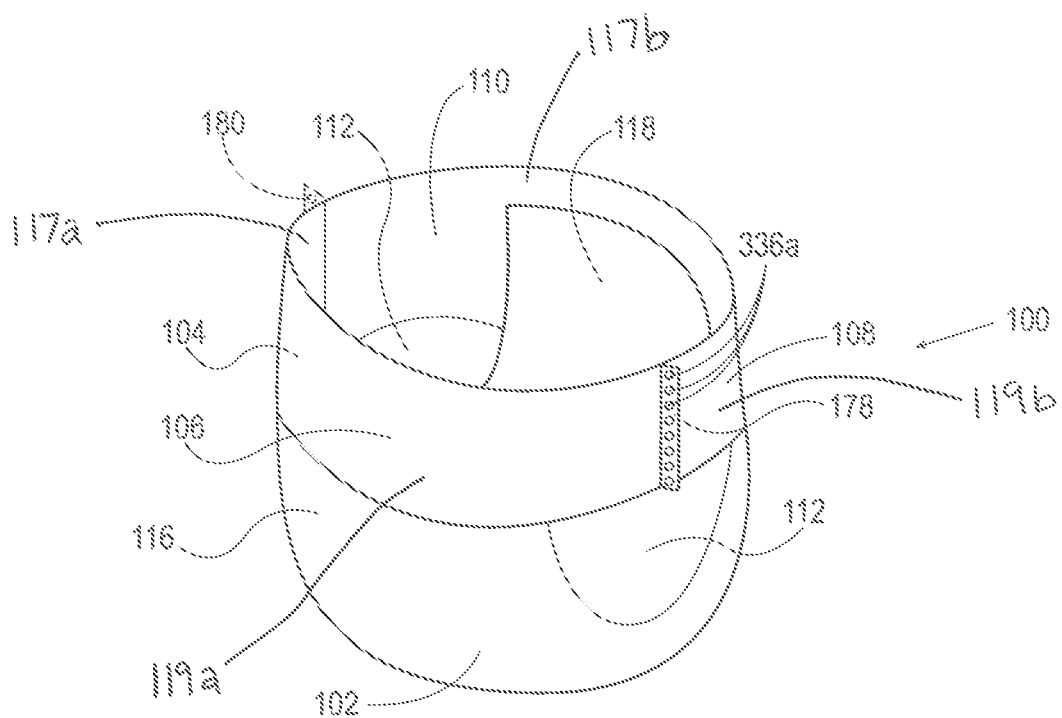
FIG. 1 is a perspective view of a diaper pant.

This application claims the benefit of U.S. Provisional Application Ser. No. 61/717,268, filed Oct. 23, 2012, the entirety of which is incorporated by reference herein.

The following definitions may be useful in understanding the present disclosure: "Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers herein to a material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

"Radial" means a direction running from the center of a drum toward an outer circumferential surface.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layered materials. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is not parallel with, and usually perpendicular to, the machine direction.

The term "pant" (also referred to as "training pant", "preclosed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed).

"Pre-fastened" refers herein to pant diapers manufactured and provided to consumers in a configuration wherein the front waist region and the back waist region are fastened or connected to each other as packaged, prior to being applied to the wearer. As such pant diapers may have a continuous perimeter waist opening and continuous perimeter leg openings designed for infant or adult wearers. As discussed in more detail below, a diaper pant can be preformed by various techniques including, but not limited to, joining together portions of the diaper using refastenable and/or permanent closure members (e.g., seams, heat bonds, pressure welds, adhesives, cohesive bonds, mechanical fasteners, etc.). In addition, pant diapers can be preformed anywhere along the circumference of the waist region (e.g., side fastened or connected, front waist fastened or connected, rear waist fastened or connected).

"Compliant" refers herein to any material with a durometer between 20 and 100 as measured according to ASTM International Designation: D2240 for Type A durometers.

The present disclosure relates to methods and apparatuses for bonding substrates together. As discussed in more detail below, the bonder apparatus may include a drum and an anvil roll adjacent the drum. The anvil roll and the drum may each include an outer circumferential surface. The drum may also include an aperture in the outer circumferential surface and one or more seaming stations located radially inward from the outer circumferential surface of the drum. The outer circumferential surface of the anvil roll may comprise a compliant material. As discussed in more detail below, the seaming station may include a fluid nozzle operatively connected with a press member. During the bonding operation, the drum is rotated about an axis of rotation and a first substrate layer advances in a machine direction onto the outer circumferential surface of the drum. A second substrate layer is also advanced in the machine direction, wherein the first substrate layer is between the second substrate layer and the drum. A fluid is heated to a temperature sufficient to at least partially melt the substrates. As the drum rotates, the fluid nozzle moves radially outward toward the aperture in the outer circumferential surface of the drum. The fluid nozzle directs a jet of the heated fluid through the aperture and onto an overlap area of the first and second substrate layers, which partially melts the overlap area. As the drum continues to rotate, the fluid nozzle retracts radially inward from the aperture, and the press member moves radially outward through the aperture.

The partially melted overlap area is then advanced through a nip formed between the press member and the anvil roll, thereby compressing the overlap area of the first and second substrates between the press member and the anvil roll. The press member may press the overlap area against the anvil roll such that the outer circumferential surface of the anvil roll is deformed radially inward toward the axis of rotation of the anvil roll. The press member may deform the outer circumferential surface of the anvil roll a radial thickness that is at least 25% of the caliper of the uncompressed, unmelted first and second substrates layers. Concurrently, the first and second substrates may be deformed in a direction that is non-tangential to the outer circumferential surface of the anvil roll and the outer surface of the press member. As a result, a discrete bond regions or seams are formed between the first and second substrates. Next, the drum continues to rotate and the press member retracts radially inward from the aperture.

It is to be appreciated that although the bonding methods and apparatuses herein may be configured to bond various types of substrates, the methods and apparatuses herein are discussed below in the context of manufacturing absorbent articles. In particular, the methods and apparatuses are discussed in the context of bonding belt substrates together to form side seams on advancing, continuous lengths of absorbent articles during production. As discussed below, an advancing continuous length of absorbent articles may include a plurality of chassis connected with a continuous first belt substrate and a continuous second belt substrate. The continuous first and second belt substrates may be separated from each other along a cross direction while advancing along a machine direction. Each chassis may extend in the cross direction and may include opposing first and second end regions separated by a central region, wherein the first end regions are connected with first belt substrate and the second end regions are connected with the second belt substrate. The chassis may also be spaced from each other along the machine direction.

A folding apparatus operates to fold the chassis around the folding axis along the central regions and to bring the second belt substrate and second end region of the chassis into a facing relationship with the first belt substrate and first end region of the chassis. In some exemplary configurations, the first belt substrate, second belt substrate, folded chassis advance in the machine direction onto the outer circumferential surface of a rotating drum such as described above. As the drum rotates, a fluid nozzle moves radially outward toward an aperture in the outer circumferential surface of the drum. The fluid nozzle directs a jet of the heated fluid through the aperture and onto an overlap area of the first and second belt substrates, which partially melts the overlap area. As the drum continues to rotate, the fluid nozzle retracts radially inward from the aperture, and the press member moves radially outward through the aperture. The partially melted overlap area is then compressed between the press member and an anvil roll, creating discrete bond sites or seams between the first and second belt substrates. The drum continues to rotate and the press member retracts radially inward from the aperture, and the continuous length of first and second belt substrates are advanced from the drum to a knife roll. The bonded regions are cut by the knife roll along the cross direction to create a first side seam on an absorbent article and a second side seam on a subsequently advancing absorbent article.

While the following discussion relates to bonding one or more substrate layers, it is to be appreciated that in some exemplary configurations, the apparatuses and methods disclosed herein may be used to emboss or deform a single substrate layer.

The processes and apparatuses discussed herein may be used to bond various types of substrate configurations, some of which may be used in the manufacture of different types of absorbent articles. To help provide additional context to the subsequent discussion of the process configurations, the following provides a general description of absorbent articles in the form of diapers that include components that may be bonded in accordance with the methods and apparatuses disclosed herein.

FIGS. 1 and 2A show an example of a diaper pant 100 that may be assembled and folded in accordance with the apparatuses and methods disclosed herein. In particular, FIG. 1 shows a perspective view of a diaper pant 100 in a pre-fastened configuration, and FIG. 2A shows a plan view of the diaper pant 100 with the portion of the diaper that faces away from a wearer oriented toward the viewer. The diaper pant 100 shown in FIGS. 1 and 2A includes a chassis 102 and a ring-like elastic belt 104. As discussed below in more detail, a first elastic belt 106 and a second elastic belt 108 are connected together to form the ring-like elastic belt 104.

With continued reference to FIG. 2A, the chassis 102 includes a first waist region 116, a second waist region 118, and a crotch region 120 disposed intermediate the first and second waist regions. The first waist region 116 may be configured as a front waist region, and the second waist region 118 may be configured as back waist region. In some configurations, the length of each of the front waist region, back waist region, and crotch region may be ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the diaper 100 and chassis 102 of FIG. 2A are shown with a longitudinal axis 124 and a lateral axis 126. In some exemplary configurations, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1 and 2A, the diaper pant 100 may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2A, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 are located longitudinally inward from the laterally extending front waist edge 121 in the front waist region 116 and the laterally extending back waist edge 122 in the back waist region 118. When the diaper pant 100 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. And the crotch region 120 may be generally positioned between the legs of the wearer with the absorbent core 142 extending from the front waist region 116 through the crotch region 120 to the back waist region 118.

Diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIG. 1.

The ring-like elastic belt 104 is defined by a first elastic belt 106 connected with a second elastic belt 108. As shown in FIG. 2A, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 116 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112. The first elastic belt 106 may define an inner surface 117a and an outer surface 119a. The second elastic belt 108 may define an inner surface 117b and an outer surface 119b.

As shown in FIGS. 2A, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 107b may also define the front waist edge 120 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some exemplary configurations, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some exemplary configurations, the first and second elastic belts include a nonwoven web of synthetic fibers, and may include a stretchable nonwoven. In other exemplary configurations, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2A, 3A, and 3B, the belt elastic material may include a plurality of elastic strands 168 which may be referred to herein as outer, waist elastics 170 and inner, waist elastics 172. As shown in FIG. 2A, the elastic strands 168 continuously extend laterally between the first and second opposing end regions 106a, 106b of the first elastic belt 106 and between the first and second opposing end regions 108a, 108b of the second elastic belt 108. In some exemplary configurations, some elastic strands 168 may be configured with discontinuities in areas, such as for example, where the first and second elastic belts 106, 108 overlap the absorbent assembly 140. In some exemplary configurations, the elastic strands 168 may be disposed at a constant interval in the longitudinal direction. In other exemplary configurations, the elastic strands 168 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt.

It is to be appreciated that the chassis 102 and elastic belts 106, 108 may be configured in different ways other than as depicted in FIG. 2A. For example, FIG. 2B shows a plan view of a diaper pant 100 having the same components as described above with reference to FIG. 2A, except the first laterally extending end edge 144 of the chassis 102 is aligned along and coincides with the outer lateral edge 107a of the first elastic belt 106, and the second laterally extending end edge 146 is aligned along and coincides with the outer lateral edge 109a of the second belt 108.

Figure 4:
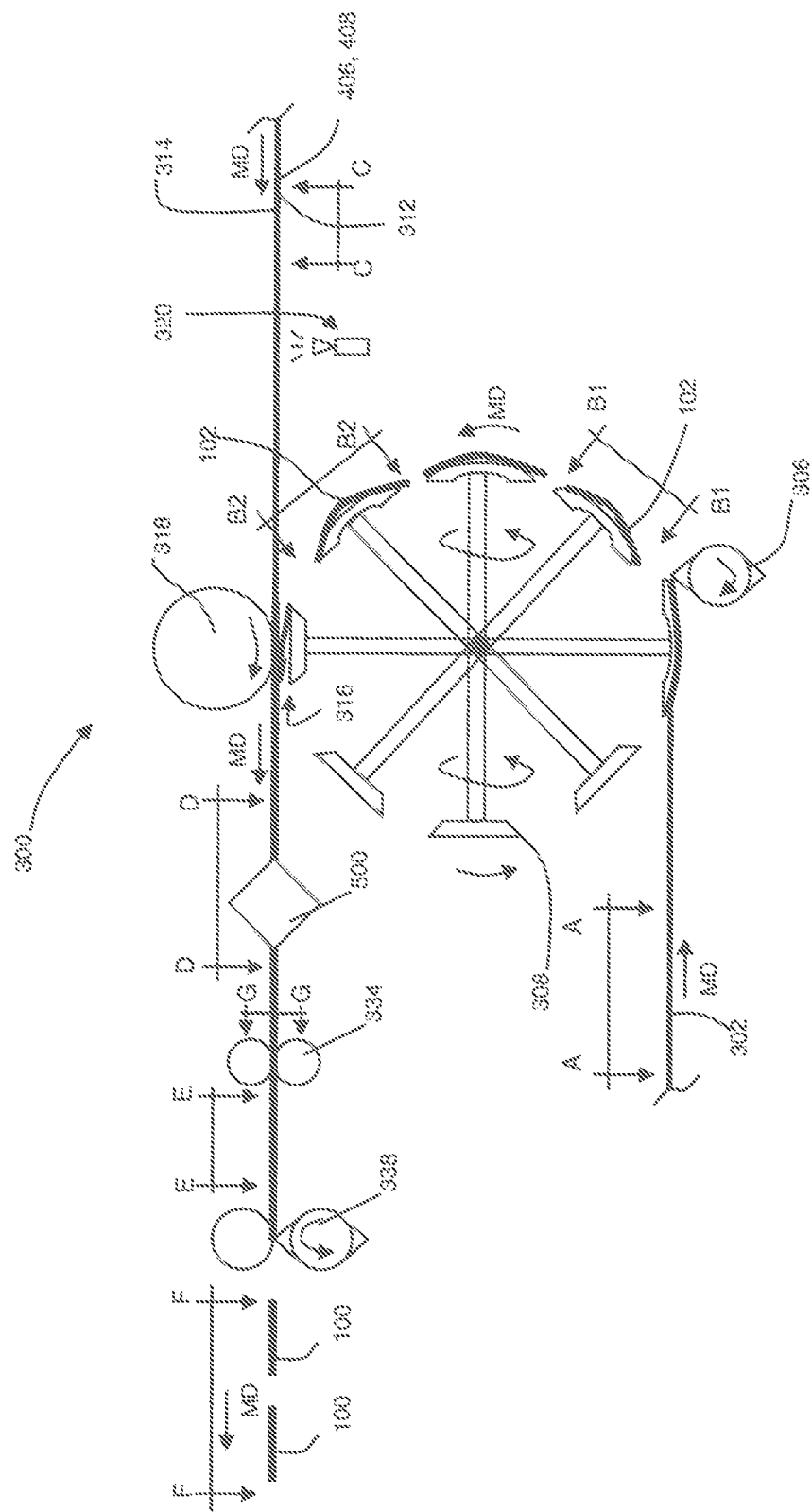
FIG. 4 is a schematic side view of a converting apparatus adapted to manufacture pre-fastened, pant diapers.

The apparatuses and methods according to the present disclosure may be utilized to assemble various components of pre-fastened, refastenable pant diapers 100. For example, FIG. 4 shows a schematic view of a converting apparatus 300 adapted to manufacture pant diapers 100. The method of operation of the converting apparatus 300 may be described with reference to the various components of pant diapers 100 described above and shown in FIGS. 1 and 2A. Although the following methods are provided in the context of the diaper 100 shown in FIGS. 1 and 2A, it is to be appreciated that various configurations of diaper pants can be manufactured according to the methods disclosed herein, such as for example, the absorbent articles disclosed in U.S. Pat. No. 7,569,039, filed on Nov. 10, 2004; U.S. Patent Publication No. 2005/0107764A1, filed on Nov. 10, 2004; U.S. patent application Ser. No. 13/221,127, filed on Aug. 30, 2011; and U.S. patent application Ser. No. 13/221,104, filed on Aug. 30, 2011.

As described in more detail below, the converting apparatus 300 shown in FIG. 4 operates to advance discrete chassis 102 along a machine direction MD such that the lateral axis of each chassis 102 is parallel with the machine direction, and wherein the chassis 102 are spaced apart from each other along the machine direction MD. Opposing waist regions 116, 118 of the spaced apart chassis 102 are then connected with continuous lengths of advancing first and second elastic belt substrates 406, 408. The chassis 102 are then folded along the lateral axis to bring the first and second elastic belt substrates 406, 408 into a facing relationship, and the first and second elastic belt substrates are connected together along regions 336, which are intermittently spaced along the machine direction. Each region 336 may include one or more discrete bond sites 336a. Then, the elastic belt substrates 406, 408 are cut along the regions 336 to create discrete diapers 100, such as shown in FIG. 1.

As shown in FIGS. 4 and 5A, a continuous length of chassis assemblies 302 are advanced in a machine direction MD to a carrier apparatus 308 and cut into discrete chassis 102 with knife roll 306. The continuous length of chassis assemblies may include absorbent assemblies 140 sandwiched between topsheet material 138 and backsheet material 136, leg elastics, barrier leg cuffs and the like. A portion of the chassis assembly is cut-away to show a portion of the topsheet material 138 and an absorbent assembly 140.

Figure 2:
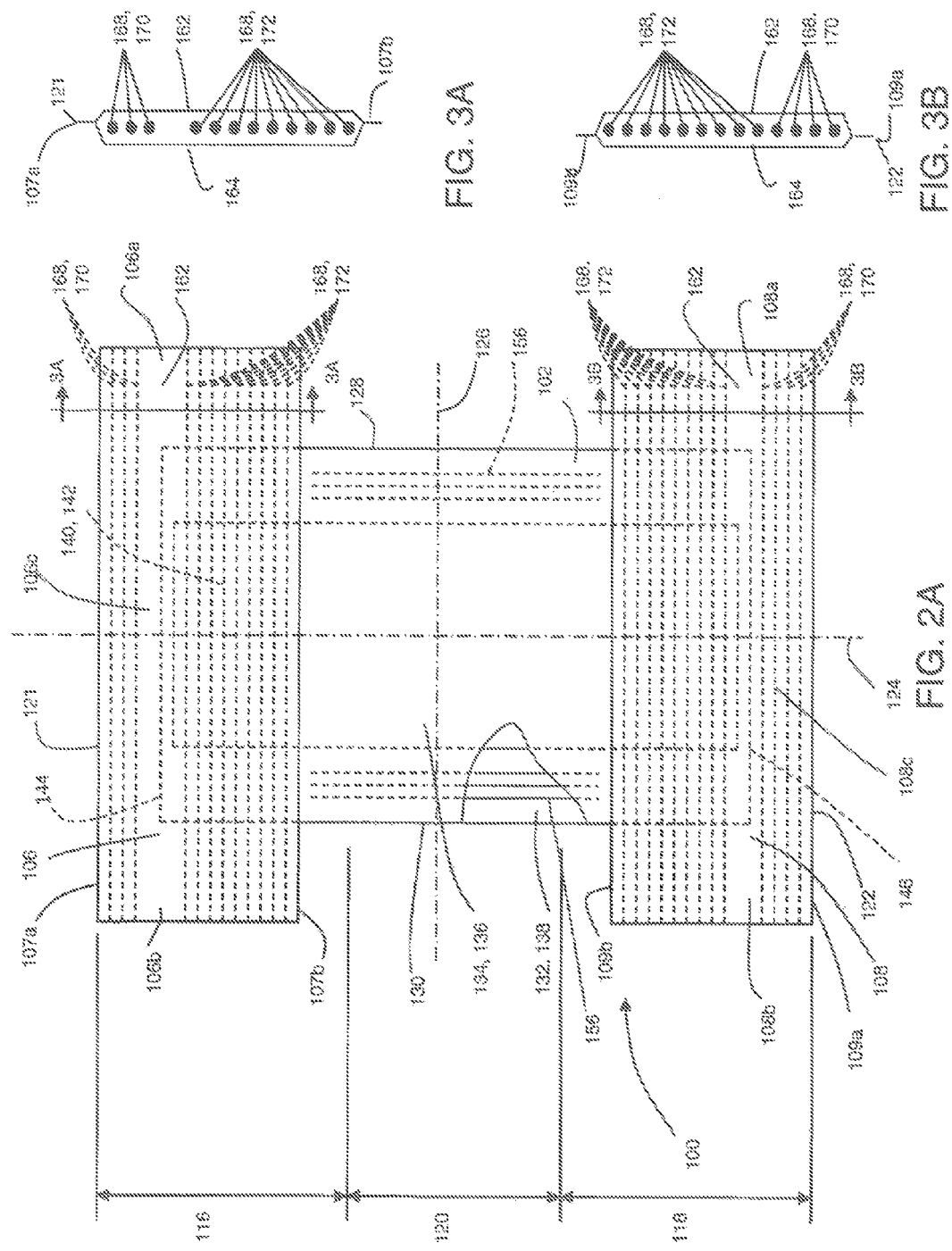
Figure 3:
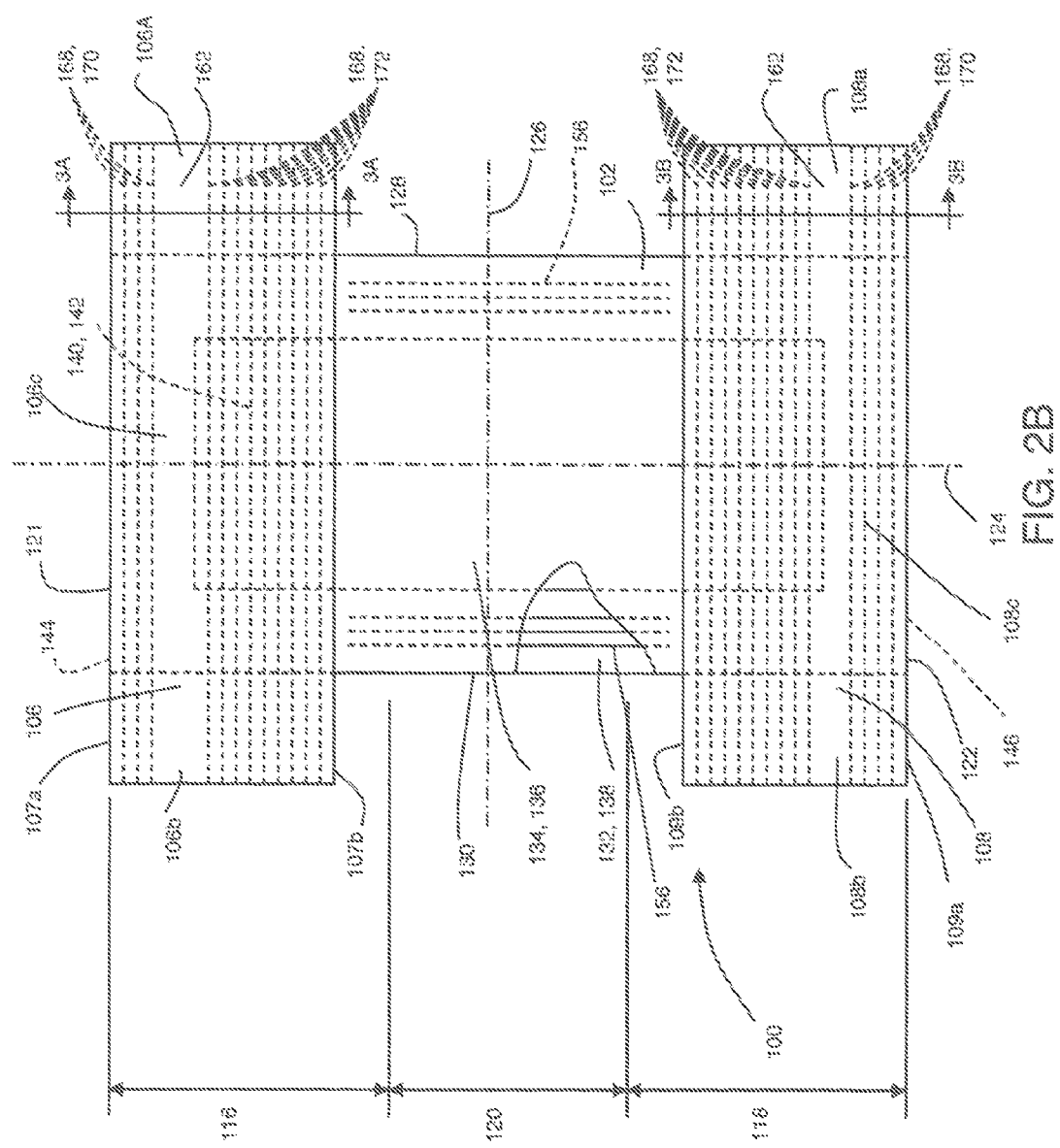
FIG. 3A is a cross-sectional view of the diaper pants of FIGS. 2A and 2B taken along line 3A-3A.
FIG. 3B is a cross-sectional view of the diaper pants of FIGS. 2A and 2B taken along line 3B-3B.

After the discrete absorbent chassis 102 are cut by the knife roll 306, the carrier apparatus 308 rotates and advances the discrete chassis 102 in the machine direction MD in the orientation shown in FIG. 5B1, wherein the longitudinal axis 124 of the chassis 102 is generally parallel with the machine direction MD. While the chassis 102 shown in FIG. 5B1 is shown with the second laterally extending end edge 146 as a leading edge and the first laterally extending end edge 144 as the trailing edge, it is to be appreciated that in other configurations, the chassis 102 may be advanced in other orientations. For example, the chassis may be oriented such that the second laterally extending end edge 146 is a trailing edge and the first laterally extending end edge 144 is a leading edge. The carrier apparatus 308 also rotates while at the same time changing the orientation of the advancing chassis 102. The carrier apparatus 308 may also change the speed at which the chassis 102 advances in the machine direction MD. It is to be appreciated that various forms of carrier apparatuses may be used with the methods herein, such as for example, the carrier apparatuses disclosed in U.S. Pat. No. 7,587,966. FIG. 5B2 shows the orientation of the chassis 102 on the carrier apparatus 308 while advancing in the machine direction. More particularly, FIG. 5B2 shows the chassis 102 with the lateral axis 126 of the chassis 102 generally parallel with the machine direction MD, and wherein the second longitudinal side edge 130 is the leading edge and the first longitudinal side edge 128 is the trailing edge.

As discussed below with reference to FIGS. 3, 5C, 5D, 5E, and 5F, the chassis 102 are transferred from the carrier apparatus 308 and combined with advancing, continuous lengths of belt substrates 406, 408, which are subsequently cut to form first and second elastic belts 106, 108 on diapers 100.

With reference to FIGS. 4 and 5C, the chassis 102 are transferred from the carrier apparatus 308 to a nip 316 between the carrier apparatus 308 and a carrier apparatus 318 where the chassis 102 is combined with continuous lengths of advancing front belt 406 and back belt 408 substrates. The front belt substrate 406 and the back belt substrate 408 each define a wearer facing surface 312 and an opposing garment facing surface 314. The wearer facing surface 312 of the first belt substrate 406 may be combined with the garment facing surface 134 of the chassis 102 along the first waist region 116, and the wearer facing surface 312 of the second belt substrate 408 may be combined with the garment facing surface 134 of the chassis 102 along the second waist region 118. As shown in FIG. 4, adhesive 320 may be intermittently applied to the wearer facing surface 312 of the first and second belt substrates 406, 408 before combining with the discrete chassis 102 at the nip 316 between roll 318 and the carrier apparatus 308.

Figure 5D:
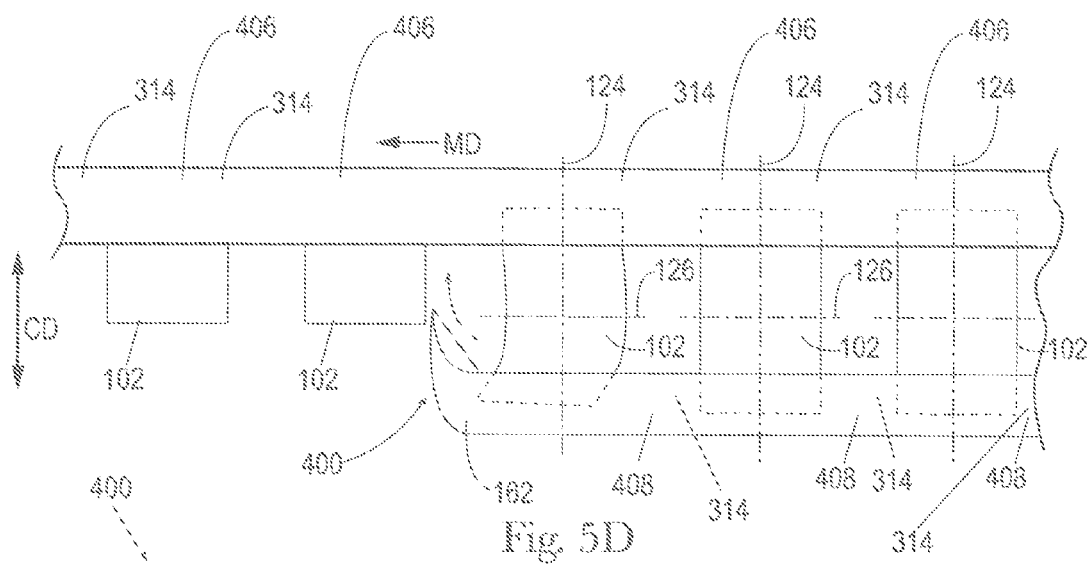
FIG. 5D is a view of multiple discrete chassis spaced from each other along the machine direction MD and connected with each other by the front and back side panel material from FIG. 4 taken along line D-D.
Figure 5E:
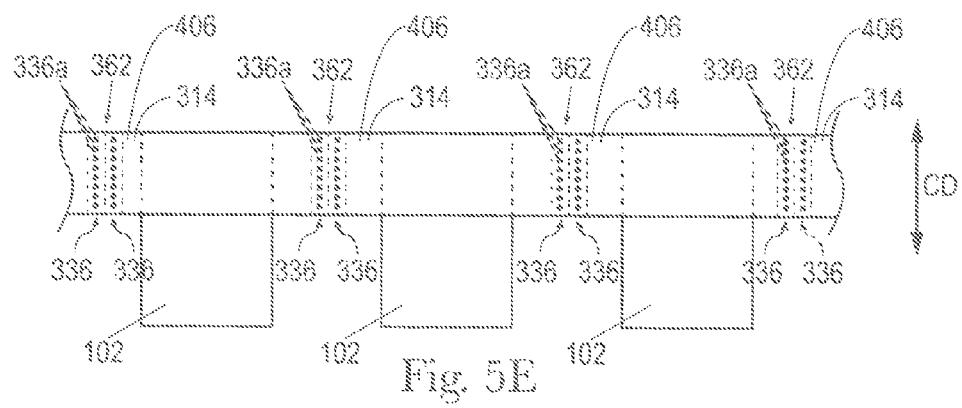
FIG. 5E is a view of folded multiple discrete chassis with the front and back side panel material in a facing relationship from FIG. 4 taken along line E-E.
Figure 5F:
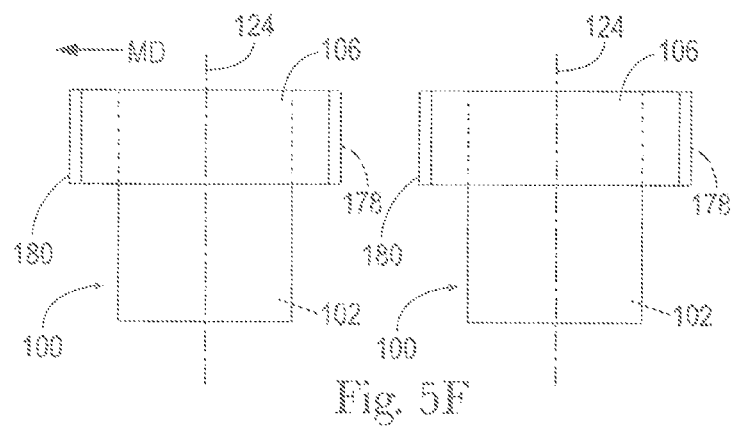
FIG. 5F is a view of two discrete absorbent articles advancing the machine direction MD from FIG. 4 taken along line F-F.
Figure 5G:
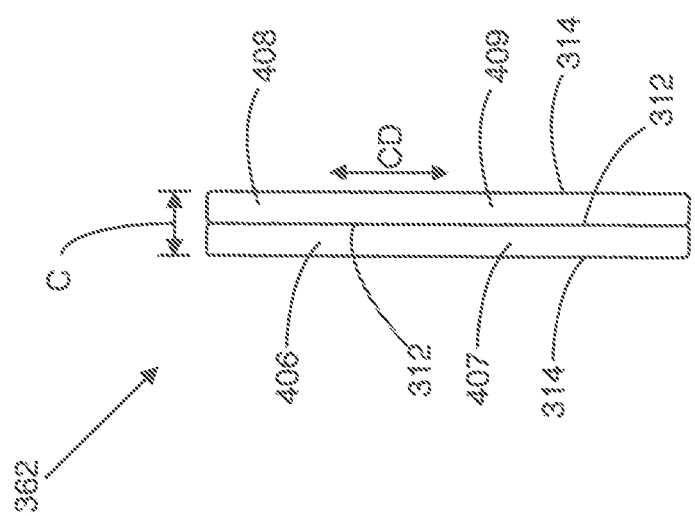
FIG. 5G is a view of an overlap area of the first and second substrates from FIG. 5D taken along line 5G-5G.

With reference to FIGS. 4 and 5D, a continuous length of absorbent articles 400 is defined by multiple discrete chassis 102 spaced from each other along the machine direction MD and connected with each other by the second belt substrate 408 and the first belt substrate 406. As shown in FIG. 4, the continuous length of absorbent articles 400 advances from the nip 316 to a folding apparatus 500. At the folding apparatus 500, each chassis 102 is folded in the cross direction CD along a lateral axis 126 to place the first waist region 116, and specifically, the inner, body facing surface 132 into a facing, surface to surface orientation with the inner, body surface 132 of the second waist region 118. The folding of the chassis also positions the wearer facing surface 312 of the second belt substrate 408 extending between each chassis 102 in a facing relationship with the wearer facing surface 312 of the first belt substrate 406 extending between each chassis 102. Referring to FIGS. 4, 5D, and 5E, the folded discrete chassis 102 connected with the first and second belt substrates 406, 408 are advanced from the folding apparatus 500 to a bonder apparatus 334. The bonder apparatus 334 operates to bond an overlap area 362, thus creating discrete bond sites 336a. The overlap area 362 includes a first substrate layer 407 and a second substrate layer 409 shown in FIG. 5G as a portion of the second belt substrate 408 extending between each chassis 102 and a portion of the first belt substrate 406 extending between each chassis 102, respectively. The overlap area 362 may be defined by a caliper C as shown in FIG. 5G. The caliper C is the combined thickness of the uncompressed, unmelted first and second substrates 406, 408 such as shown in FIG. 5G. Referring to FIGS. 4 and 5F, a continuous length of absorbent articles are advanced from the bonder 334 to a knife roll 338 where the regions 336 are cut into along the cross direction to create a first side seam 178 on an absorbent article 100 and a second side seam 180 on a subsequently advancing absorbent article.

Although the absorbent article is described as having a first and second belt substrate, it is to be appreciated that the absorbent article may have only one belt substrate. Further, it is to be appreciated that the chassis and belt substrate of the absorbent article may be one continuous substrate such that the overlap area is formed from the same substrate. As such, the bonder apparatus may operate to bond a continuous substrate at an overlap area to form one or more discrete bond sites.

Figure 6B:
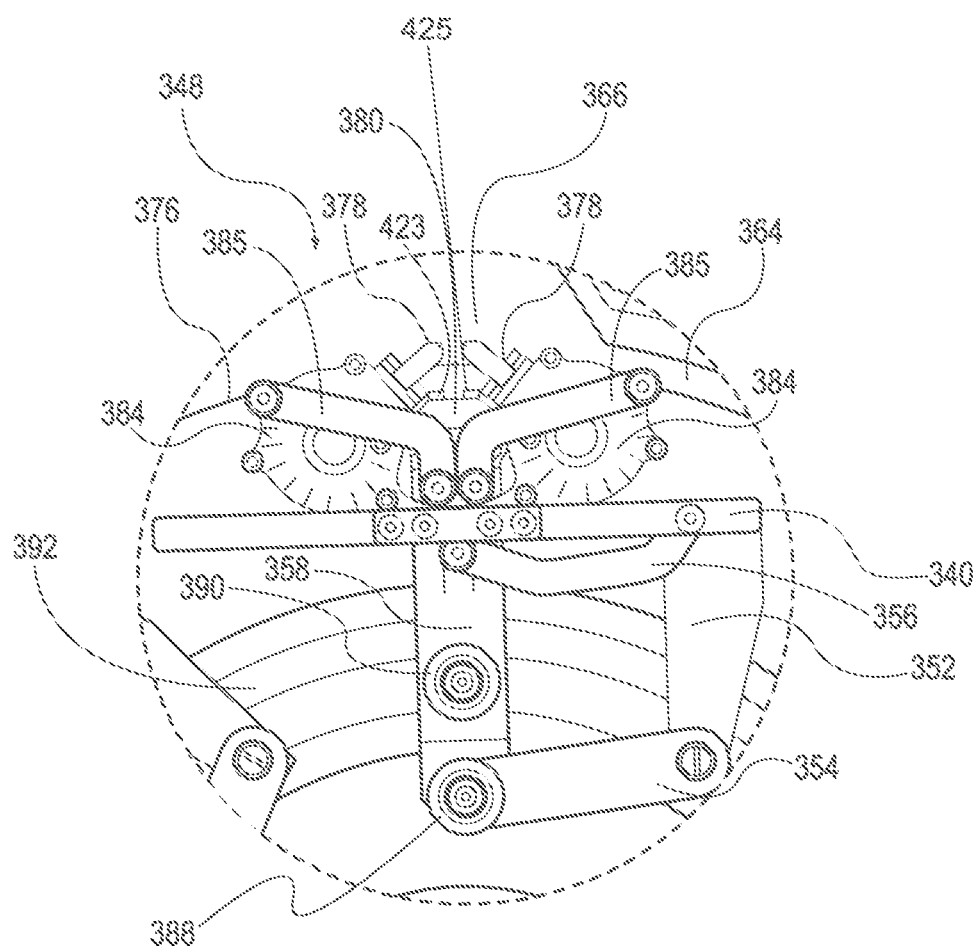
FIG. 6B is an elevation view of the seamer station of FIG. 6A.

With reference to FIG. 4, the converting apparatus may include a bonder apparatus 334. For example, FIG. 6A shows a detailed schematic side view of a bonder apparatus 334 that may be used with the methods and apparatuses herein. As shown in FIG. 6A, the bonder apparatus 334 may include a drum 364 and an anvil roll 368 located adjacent the drum 364. The anvil roll 368 includes an outer circumferential surface 370 and is adapted to rotate about an axis of rotation 372. The anvil roll 368, including the outer circumferential surface 370, may comprise a compliant material. The drum 364 may also include an outer circumferential surface 376 and is adapted to rotate about an axis of rotation 374. The drum 364 may include one or more drum apertures 366 in the outer circumferential surface 376. In addition, a plurality of seaming stations 348 are positioned radially inward from the outer circumferential surface 376 and the drum apertures 366. As discussed in more detail below, with reference to FIG. 6B, each seaming station 348 may include a fluid nozzle 378 and a press member 380. Although the drum 364 shown in FIG. 6A includes six seaming stations 348, it is to be appreciated that the drum 364 may be configured to include more or less than six seaming stations 348.

During operation, the drum 364 may rotate about the axis of rotation 374 and the anvil roll 368 may rotate about the axis of rotation 372 in the directions shown in FIG. 6A. Absorbent articles 400 may advance in machine direction MD onto the outer circumferential surface 376, wherein the first belt substrate 406 is between the second belt substrate 408 and the outer circumferential surface 376. As the drum 364 rotates, fluid nozzles 378 of a seaming station 348 move radially outward toward the drum aperture 366 in the outer circumferential surface 376 as shown in FIG. 6B. A fluid is heated to a temperature sufficient to at least partially melt the overlap area. The fluid nozzles 378 direct a jet of the heated fluid through the drum aperture 366 and onto an overlap area of the first and second substrates 406, 408 to partially melts the overlap area.

Referring to FIGS. 6A and 6B, as the drum 364 continues to rotate, the fluid nozzles 378 retract radially inward from the drum aperture 366, the drum 112 continues to rotate about the axis of rotation 374, and a press member shifts radially outward through the drum aperture 366. The absorbent articles 400 then pass through a nip 332 formed between the press member 380 and the anvil roll 368 as shown in FIG. 6A. The press member 380 compresses the partially melted overlap area against the outer circumferential surface 370, creating one or more discrete bond sites 336a between the first and second belt substrates 406, 408. As the press member 380 compresses the partially melted overlap area against the outer circumferential surface 370, the press member 380 may deform the outer circumferential surface 370 of the anvil roll 368 radially inward toward the axis of rotation 372. Concurrently, the overlap area of the first and second substrates 406, 408 is deformed in a direction Z that is non-tangential to the outer surface 425 of the press member 380 and the outer circumferential surface 370 of the anvil roll 368, as described in more detail below. As a result, the press member 380 compresses the overlap area for more than an instant in time as the absorbent articles 400 advance through the nip 332. The drum 364 continues to rotate and the press member retracts radially inward from the drum aperture 366.

Figure 7:
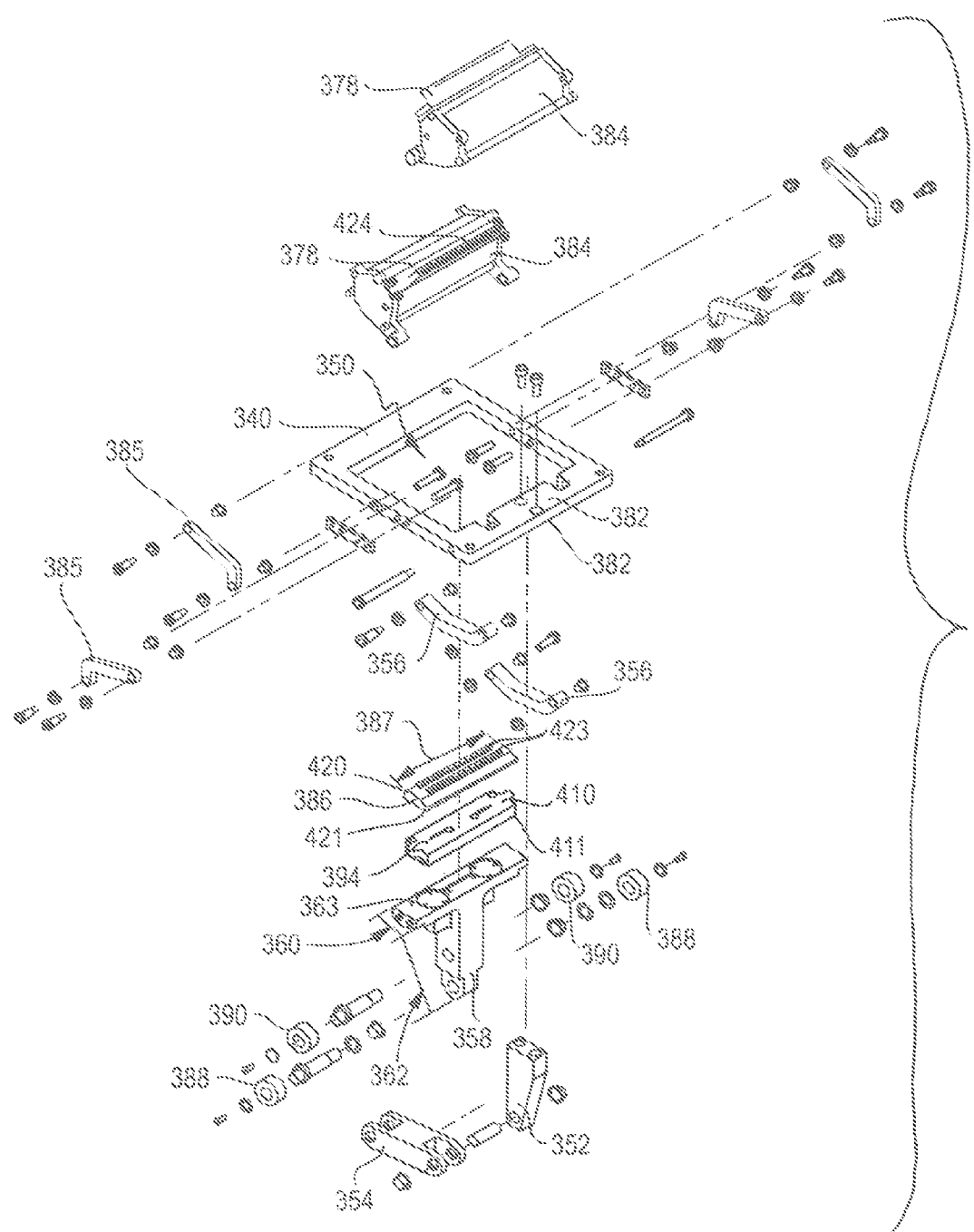
FIG. 7 is a detailed, exploded view of a seaming station.

Each seaming station of the drum may include a fluid nozzle and a press member. FIG. 7 shows a detailed exploded view of a seaming station 348. As shown in FIG. 7, the seaming station 348 includes a base member 340 that is immovably connected with and rotates with the drum. The base member 340 is substantially square shaped and is defined by a base member top surface 382 and a base member bottom surface 383. The base member 340 includes a base aperture 350 extending through the base member top and bottom surfaces 382, 383 such that a fluid nozzle 384 and press member 380 may extend through the base aperture 350. Moreover, the base member bottom surface 383 is immovably connected with a base link 352. As discussed below, one end of the base link 352 is connected to the base member bottom surface 383, and another end of the base link 352 is operatively connected to a first shifting link 354.

With continuing reference to FIG. 7, the seaming station 348 also includes a cam follower member 358 and first and second sets of cam rollers 388, 390 rollingly connected with the cam follower member 358. The cam follower member 358 is substantially T-shaped, and is defined by a cam follower member first portion 360, a cam follower member second portion 362, and a cam follower member top face 363. The cam follower member first portion 360 is operatively connected with the first shifting link 354 and the first set of cam rollers 388 at the same position on the cam follower member 358. Furthermore, the second set of cam rollers 390 is operatively connected to the cam follower member second portion 362 at a position radially outboard from the first set of cam rollers 388. Also operatively connected to the cam follower member 358 is a set of second shifting links 356. The set of second shifting links 356 operatively connects the base member 340 to the cam follower member first portion 360 at a position relatively outboard of the second set of cam rollers 390.

As discussed in more detail below, with reference to FIGS. 6A1 and 6B, the first and second set of cam rollers 388, 390 are configured to roll along a stationary cam track as the drum 364 rotates. The stationary cam track 293 surrounds the axis of rotation 374 and is defined by an inner circumferential surface 395 and a radius R that extends from the inner circumferential surface 395 of the stationary cam track 392 to the axis of rotation 374 as shown in FIG. 6A1. In some exemplary configurations, the stationary cam track 392 may include various curved and/or straight regions such that the stationary cam track 392 is defined by relatively longer and shorter radii R at different points along the inner circumferential surface 395 of the stationary cam track 392. First and second sets of cam rollers 388, 390 roll on the stationary cam track 392 as the drum 364 rotates. The first, second, and third shifting links 354, 356, 385 pivot where the radius R of the stationary cam track 392 increases or decreases as the first and second set of cam rollers 388, 390 roll along the stationary cam track 392. At the same time, in regions where the stationary cam track 392 is defined by relatively longer radii, R, the cam follower member 385 shifts radially outward through the base aperture. Whereas, in regions where the stationary cam track 392 is defined by relatively shorter radii, R, the cam follower member shifts radially inward through the base aperture. It is to be appreciated that the cam track 392 may be configured to have various other shapes and sizes. For example, in some exemplary configurations, the cam track 392 may be configured to have a circular shape that is offset or eccentric with respect to the axis of rotation 374. Offsetting the stationary cam track from the axis of rotation causes the cam follower member to shift as the first and second sets of cam rollers roll along the stationary cam track.

Figure 8:
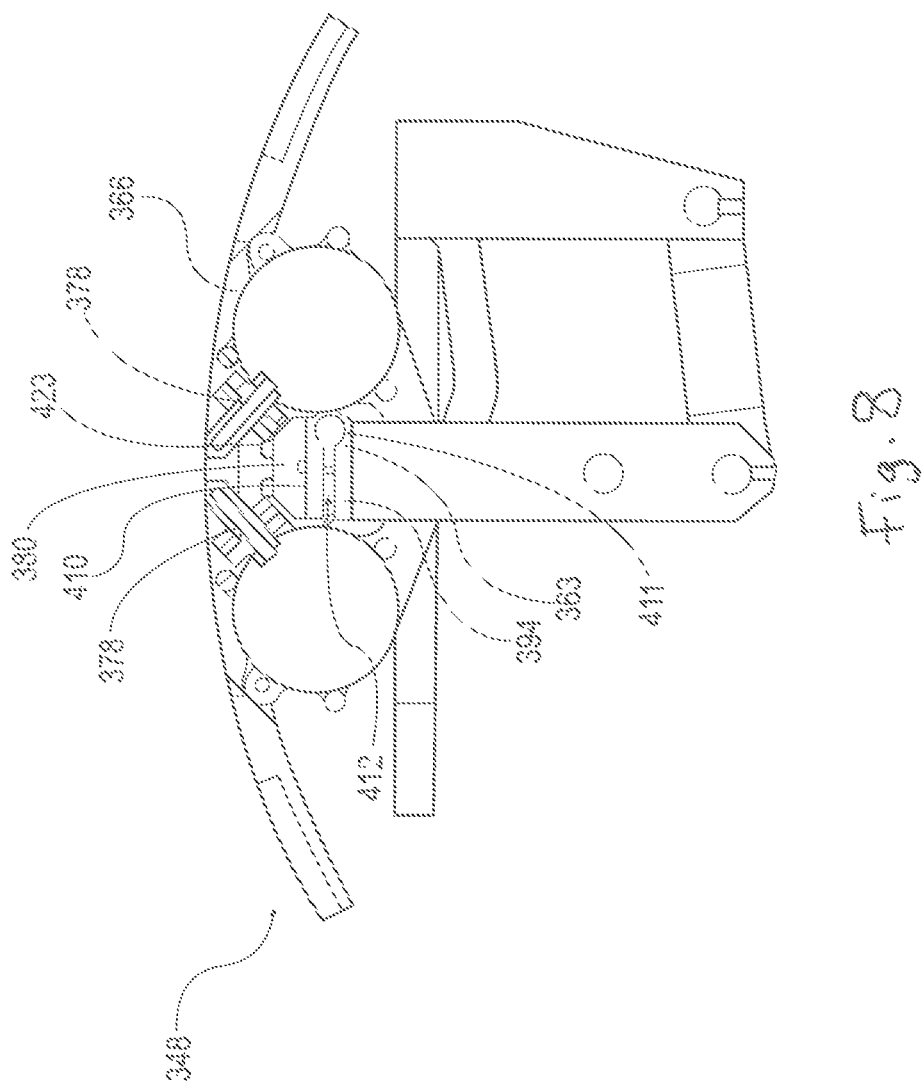
FIG. 8 is an elevation view of a seaming station.

With reference to FIGS. 7 and 8, the seaming station 348 may further include a spring member 394. The spring member 394 may be substantially U-shaped and defined by a spring member top face 410, a spring member bottom face 411, and a spring member side opening 412. With reference to FIG. 7, the spring member bottom face 411 is fixedly connected to the cam follower member top face 363. The spring member 394 may extend along the entirety of the cam follower member top face 363. As discussed in further detail below, the spring member side opening 412 allows the spring member 394 to flex as a press member compresses the partially melted overlap area against the outer circumferential surface.

The seaming station may also include a press member 380 as shown in FIG. 7. The press member 380 may be substantially rectangular in shape and defined by a press member top face 420, a press member bottom face 421, and a press member length 387. The press member 380 may include substantially square-shaped projections 423 extending outwardly from the press member top face 420. The projections 423 may be defined by an outer surface 425 that is the most radially outboard surface of the projection 423. In some exemplary configurations, the projections 423 may have a flat outer surface 425 as shown in FIG. 6B. However, in other exemplary configurations, the projections 423 may have a curved outer surface. The press member bottom face 421 is immovably connected to the spring member top face 410. The press member 380 may extend along the entirety of the spring member top face 410. As discussed in more detail below, the projections 423 may be arranged into two rows as shown in FIG. 7. The projections 423 may include a compliant material that may form the outer surface 425 of the projections 423.

With continuing reference to FIG. 7, the seaming station 348 may also include heating apparatuses 384. As discussed in more detail below, each heating apparatus 384 provides a pressurized fluid source for delivery of heated, pressurized fluid, such as air for example, to the fluid nozzle 378. In some exemplary configurations, a valve may control egress of the fluid from the heating apparatus 384 and into a fluid nozzle 378. Each heating apparatus 384 is operatively connected to the base member 340 by a set of third shifting links 385. Each third shifting link 385 is operatively connected to one end of one heating apparatus 384 and also to the cam follower member second portion 365.

With reference to FIG. 7, the seaming station may also include a fluid nozzle 378. The fluid nozzle 378 may include one or more fluid orifices 424 where the heated, pressurized fluid is released from the fluid nozzle 378. Each heating apparatus 384 is immovably connected with a separate fluid nozzle 378. As shown in FIG. 7, the fluid orifices 424 may be circular and may extend in a row along the fluid nozzle 378.

Figure 9:
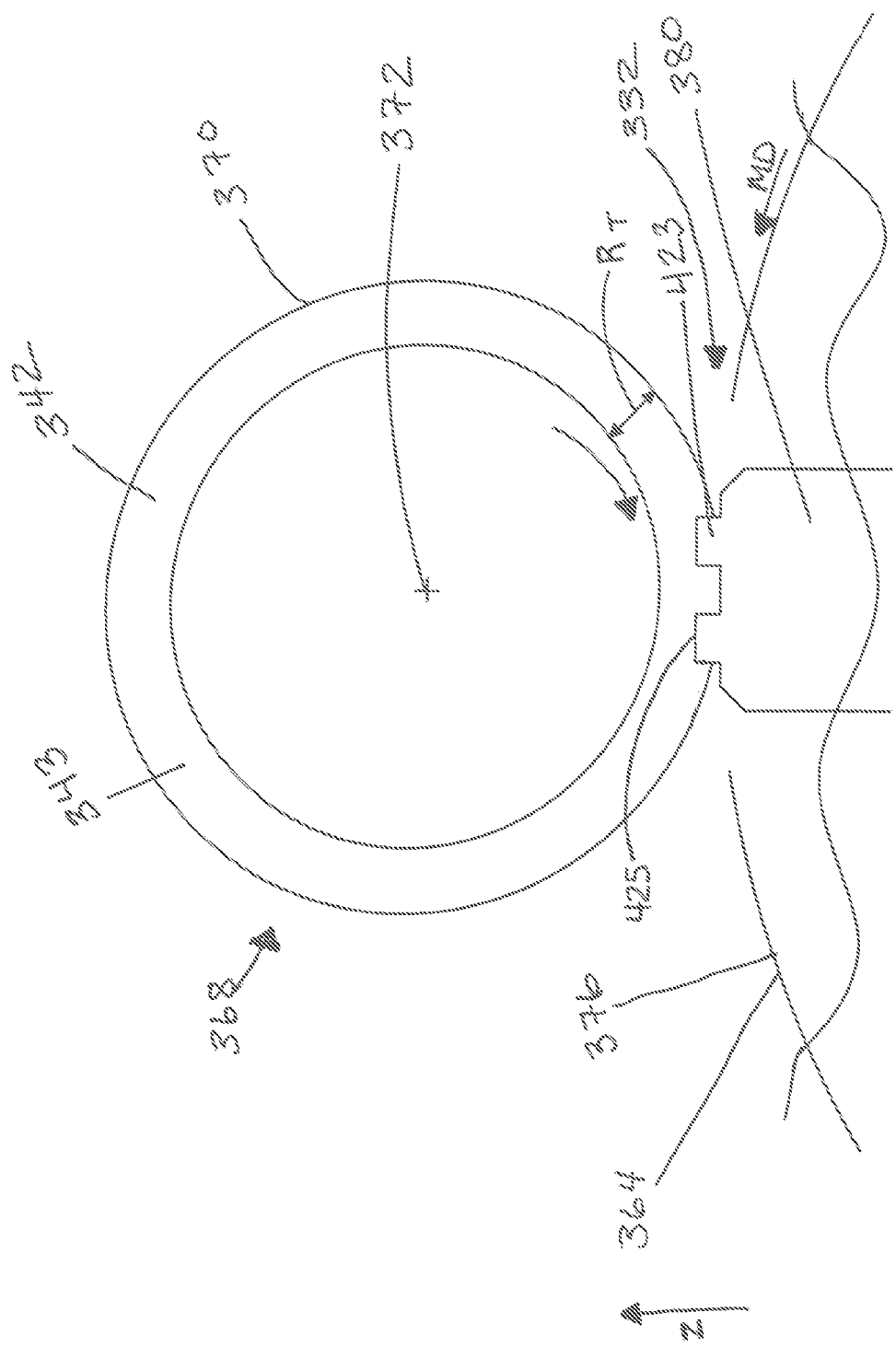
FIG. 9 is a partial, side elevation view of a press member and an anvil roll that is configured to deform first and second substrate layers in a z-direction.

Referring to FIGS. 6A and 9, the anvil roll 368 may include a compliant material 342. The compliant material 342 may define the outer circumferential surface 370 of the anvil roll 368. The compliant material may include, for example, silicone, natural rubber, synthetic rubber (e.g., Buna-N, Buna-S, nitrile, and neoprene), polyurethanes, ABS plastic. The compliant material may have a durometer within the Shore A scale range of 20-100 durometer or an equivalent durometer. In some exemplary configurations, the compliant material 342 may form a sleeve 343 on the anvil roll 368 as shown in FIG. 6A. The sleeve 343 may define the outer circumferential surface 370 of the anvil roll 368. In some exemplary configurations, the anvil roll 368 may be comprised entirely of a compliant material.

In operation, absorbent articles are advanced in the machine direction MD to a bonder apparatus 334. With reference to FIG. 6A, the absorbent articles 400 advance in the machine direction MD onto the outer circumferential surface 376 as the drum 364 is rotating about the axis of rotation 374. The first belt substrate 406 is between the second belt substrate 408 and the outer circumferential surface 376. More particularly, the outer layer 162 of the first belt substrate 406 may be in direct contact with the outer circumferential surface 376. And the inner layer 164 of the first belt substrate 406 may be in direct contact with the inner layer 164 of the second belt substrate 408. The outer circumferential surface 376 is traveling at the same speed as the advancing absorbent articles 400 such that the position the absorbent articles 400 are received on the outer circumferential surface 376 remains constant until the absorbent articles 400 are removed from the drum 364 downstream. The overlap area of the first and second belt substrates 406, 408 is positioned on the outer circumferential surface 376 coincident with a drum aperture 366. As discussed in more detail below, a seaming station 348, located radially inward from the drum aperture 366, is configured to bond a portion of the overlap area as the absorbent articles 400 travel along the drum 364. The seaming station 348 is arranged in a first configuration as the absorbent articles are received on the drum 364.

FIG. 10 shows a perspective view of a seaming station 348 in a first configuration. With reference to FIGS. 8 and 10, in the first configuration, the fluid nozzles 378 are positioned radially outward near the drum aperture 366 and outer circumferential surface 376, while the press member 380 is positioned radially inward, away from the drum aperture 366 and the outer circumferential surface 376. In addition, the fluid nozzles 378 are positioned at the same circumferential location as the projections 423 of the press member 380, such that the heated fluid is directed to the same locations on the overlap area that will subsequently be compressed by the press member 380.

With reference to FIGS. 6A and 6B, as the drum 364 continues to rotate, the absorbent articles 400 wrap around the outer circumferential surface 376. At the same time, a jet of heated, pressurized fluid is directed from the heating apparatuses 384 out of the fluid nozzles 378 and onto the overlap area of the first and second belt substrates 406, 408. The fluid nozzles 378 are maintained a preselected distance Y from the outer layer 162 of the first belt substrate 406 to control the pressure applied to the overlap area by the heated fluid as shown in FIG. 6B1. In some exemplary configurations, the distance Y between the outer layer 162 of the first belt substrate 406 and the fluid nozzles 378 may be maintained within 3 mm of the preselected distance Y.

A position control apparatus may be used to maintain the absorbent articles within a constant distance from the outer circumferential surface of the drum as the fluid is heating the overlap area. In some exemplary configurations, the position control apparatus 450 may be a belt apparatus 451 as shown in FIG. 11. The position control apparatus 450 may be located adjacent the drum 364 and may take the shape of at least a portion of the outer circumferential surface 376. The position control apparatus may hold the absorbent articles 400 in the range of 0 millimeters to about 10 millimeters from the outer circumferential surface of the drum, or between about 0.5 millimeters to about 5 millimeters from the outer circumferential surface.

Once the overlap area is at least partially melted, and as the drum 364 continues to rotate, the seaming station shifts to a second configuration. With reference to FIGS. 6A, 6A1, 6B, and 6B1, the first and second sets of cam rollers 388, 390 roll on the stationary cam track 392 as the drum 364 rotates. The stationary cam track 392 remains stationary while the first and second set of cam rollers 388, 390 roll along the stationary cam track 392. As the first and second sets of cam rollers 388, 390 roll from regions where the radius R of the stationary cam track 392 is defined by relatively shorter radii R to regions where the radius R of the stationary cam track 392 is defined by relatively longer radii R, the first, second, and third shifting links 354, 356, 385 pivot. With reference to FIG. 6B, the first shifting link 354 pivots at the base link 352 and at the cam follower member 358, while the set of second shifting links 356 pivot at the cam follower member 358 and at the base member 340. At the same time, the cam follower member 358 shifts radially outward toward the outer circumferential surface 376. The third shifting links 385 also pivot at the cam follower member 358, causing the heating apparatuses 384 to move radially inward, away from the outer circumferential surface 376, and causing the fluid nozzles 378 to spread circumferentially apart from each other on either side of the press member 380. The seaming station 348 continues to shift until the first and second set of cam rollers 388, 390 roll along regions of the stationary cam track 392 where the radius R of the stationary cam track 392 remains constant, which corresponds to the second configuration of the seaming station 348. The seaming station 348 remains in the second configuration until the first and second set of cam rollers 388, 390 travel along the stationary cam track 392 to regions where the stationary cam track is defined by relatively shorter radii.

FIG. 12 shows a perspective view of a seaming station 348 in the second configuration. With reference to FIG. 12, at the second configuration, the press member 380 is extending through the drum aperture beyond the outer circumferential surface, the heating apparatuses 384 are positioned radially inward, away from the drum aperture 366, and the fluid nozzles 378 are located on either side of the cam follower member adjacent to the outer circumferential surface 366.

With reference to FIGS. 6A and 6B, while the drum 364 continues to rotate and the seaming station 348 is in the second configuration, the partially melted overlap area approaches the anvil roll 368 located adjacent the drum 364. As the absorbent articles 400 advances through the nip 332 formed between the anvil roll 368 and drum 364, the press member 380, which is extending radially outward from the drum aperture 366, compresses the partially melted overlap area against the outer circumferential surface 370. As shown in FIGS. 9 and 13-15, as the absorbent articles 400 advance through the nip 332 between the rotating anvil roll 368 and the press member 380 of the seaming station 348, the projections 423 of the press member 380 deform the outer circumferential surface 370 of the anvil roll 368 radially inward toward the axis of rotation 372. As a result, the first and second substrates 406, 408 deform in a direction, Z, that is non-tangential to the outer circumferential surface 370 of the anvil 368 and the outer surface 425 of the projections 423 of the press member 380.

The anvil roll 368 may be configured to deform in a direction toward the axis of rotation 372 by a radial thickness $R_T$ that is at least 25% of the caliper, C, of the combined, uncompressed and unmelted first and second substrates 406, 408. In some exemplary configurations, the anvil roll 368 may deform by a radial thickness $R_T$ that is at least 30%, at least 40%, at least 50%, at least 60%, at least 70%, at least 80% of the caliper, C, of the combined, uncompressed and unmelted first and second substrates 406, 408.

The projections 423 of the press member 380 are configured to contact the same locations of the overlap area that were at least partially melted by the heated fluid as shown in FIG. 6B, thus forming discrete bond sites 336a in the overlap area. The spring member 394 may be used to apply a predetermined force to the overlap area between the press member 380 and the anvil roll 368. Once compressed, the absorbent articles advance off of the drum outer circumferential. The drum continues to rotate and the seaming station shifts back to the first configuration in order to form discrete bond sites in a subsequent absorbent article.

In some exemplary configurations, the distance from the absorbent articles to the fluid nozzles may range from 0 millimeters to about 20 millimeters, or between about 0 millimeters and about 5 millimeters for example, or between about 0.5 millimeters and about 3 millimeters. Control of the distance between the first and second substrate and the fluid orifice 424 may also result in a relatively more predictable fluid spray and melt pattern during the heating process.

The heated fluid may include ambient air or other gases. It is to be appreciated that the fluid may be heated to various temperatures and pressurized to various pressures. For example, in some exemplary configurations, the fluid may be heated up to a temperature ranging from the lower melting point of first and second belt substrates minus 30° C. to the lower melting point of the first and second belt substrates plus 100° C. In some exemplary configurations, the fluid pressure may range from $0.1 \times 10^5$ Newtons per square meter to $1 \times 10^6$ Newtons per square meter. In some exemplary configurations, the heated fluid may be directed toward at least one of the first and second belt substrates for a time interval ranging from 10 to 1000 milliseconds or greater. Shorter or greater time intervals may be used.

In some exemplary configurations, the press member may compress the partially melted overlap area against the outer circumferential surface at a pressure in the range of about $1 \times 10^5$ Newtons per square meter to about $1 \times 10^8$ Newtons per square meter. In some exemplary configurations, the press member 366 may compress the first and second belt substrates for a time period ranging from 10 to 1000 milliseconds or greater. Shorter or greater time intervals may be used.

Referring to FIG. 10, it is to be appreciated that the projections 423 may be regularly or irregularly spaced in various configurations and may be oriented in various directions. The projections 423 may have a circular, oval, or various other shapes. In some exemplary configurations, the projections of the press member may have a smooth surface such that the discrete bond sites will be flat. However, in some exemplary configurations, the projections of the press member may have a rough surface such that the discrete bond sites will have a texture. With reference to FIG. 10, the projections 423 may have a height 440 in the range of about 0.5 millimeters to about 5 millimeters. In some exemplary configurations, the projections may have a width 442 in the range of about 2 millimeters to about 10 millimeters, or between about 4 millimeters to about 6 millimeters.

While it is shown in FIGS. 8 and 12 that the spring member 390 has a U-shape, it is to be appreciated that various other spring members may be used to absorb pressure from the press member 380 compressing the overlap area between the outer circumferential surface. By controlling the amount of force applied to the overlap area, it is possible to apply a force sufficient to form discrete bond sites to minimize damage to the substrates and/or forming relatively weak discrete bonds.

The temperature and pressure of the fluid are maintained within a specified range once the nominal set points are selected. For example, a set point may be selected from the ranges discussed above, and the temperature may then be maintained in a fixed range around the nominal set point, such as ±30° C., and the pressure may be maintained in a fixed range around the nominal set point, such as ±1 bar. The acceptable range will depend on the relationship between the properties, such as softening point and/or melting temperature, of the materials to be joined and the nominal set point selected. For example, a nominal set point above the melting temperature of one or more of the materials to be joined may require a tighter control range than a nominal set point well below the melting temperature of one or more material to be joined. The control range may be asymmetrical about the nominal set point. By sufficiently heating, it is meant that the fluid is heated to a temperature that will enable at least partial melting, or at least softening, of the substrate or substrates. Sufficient heating may vary with the materials and equipment used. For example, if the heated fluid is applied to the substrate or substrates almost immediately, with little or no time to cool, the fluid may be heated to approximately the softening point or approximately the melting point of the substrate or substrates. If the heated fluid is directed to the substrate or substrates over some gap in time or distance, such that the heated fluid may cool somewhat before interacting with the substrate or substrates, it may be necessary to heat the fluid above, possibly significantly above, the softening point or melting point of the substrate or substrates.

The duration of energy transfer in the process described herein may be a dynamic process, and may create a temperature gradient across the meltable components' cross sections. That is, the core of the meltable components may remain solid while the exterior surface of the meltable components melt or come close to melting. Even below the melting temperature, the exterior surface may reach a softening point, such that plastic deformation of the material may occur at a much lower load than for the same material at ambient temperature. Thus, if one or more of the materials to be joined have a softening point, the process may be adjusted to achieve a temperature in at least a portion of first and second belt substrates 406, 408 between the softening point and the melting point. The use of a temperature at or above the softening point but below the melting point of one or more of the meltable components may allow for the creation of a strong bond between first and second belt substrates 406, 408 with reduced disruption to the structure of the meltable components e.g., attenuating or otherwise weakening the meltable components.

With reference to FIGS. 4 and 5F, once the discrete bond sites 336a are formed, the absorbent articles 400 advance in the machine direction MD to a knife roll 338 where the regions 336 are cut into along the cross direction to create a first side seam 178 on an absorbent article 100 and a second side seam 180 on a subsequently advancing absorbent article.

In some exemplary configurations, it is to be appreciated that the knife roll may be integral with the press member such that as the press member compresses the overlap area, the press member also cuts the overlap area.

Figure 17:
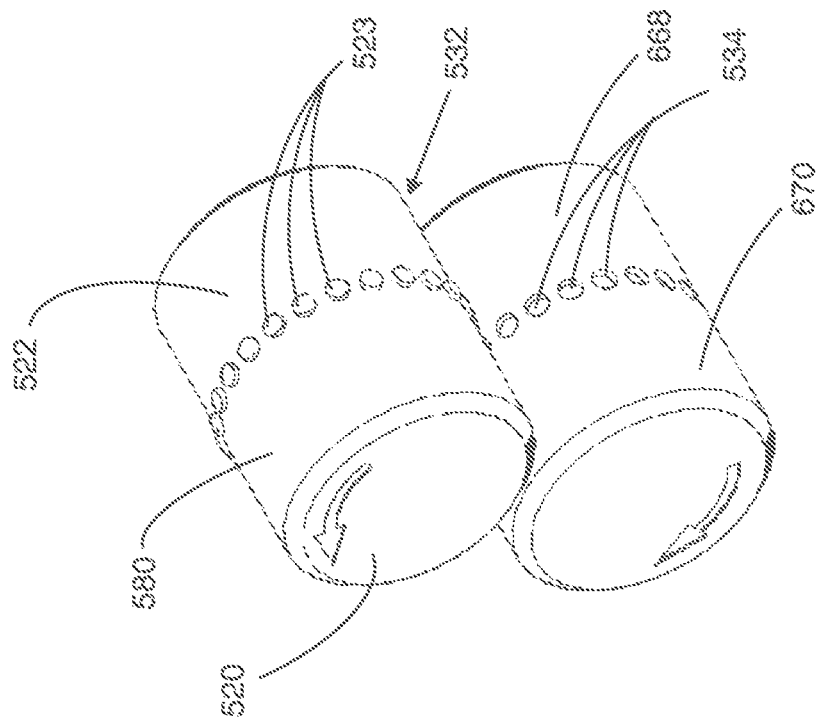
FIGS. 16-19 are perspective side views of a bonder apparatus adapted to seam pre-fastened pant diapers.
Figure 16:
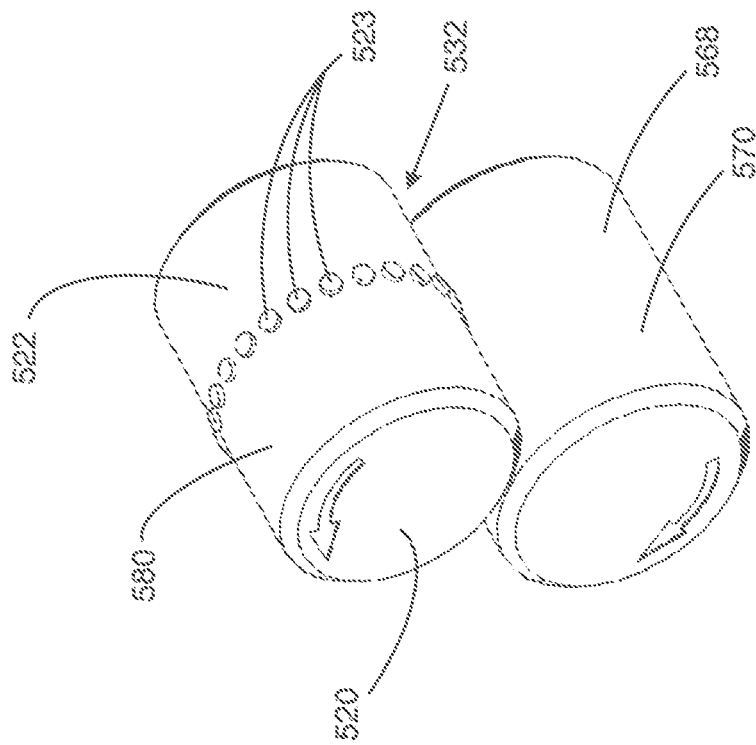

In some exemplary configurations, a press member 580 may be in the form of a rotary drum 520. As shown in FIG. 16, the rotary drum 520 may have an outer circumferential surface 522 and a plurality of projections 523 extending radially outward from the outer circumferential surface 522 of the rotary drum 520. In such an exemplary configuration, an anvil roll 568 having an outer circumferential surface 570 may be located adjacent to the rotary drum 520, forming a nip 532 there between. The anvil roll 568 may comprise a compliant material. In other exemplary configurations, an anvil roll 668 may have a plurality of apertures 534 in an outer circumferential surface 670 such as shown in FIG. 17. The apertures 534 may be configured to mate with the projections 523 of the rotary drum 520. In some exemplary configurations, the anvil roll 668 shown in FIG. 17 may be made of a rigid material, such as metal.

Figure 19:
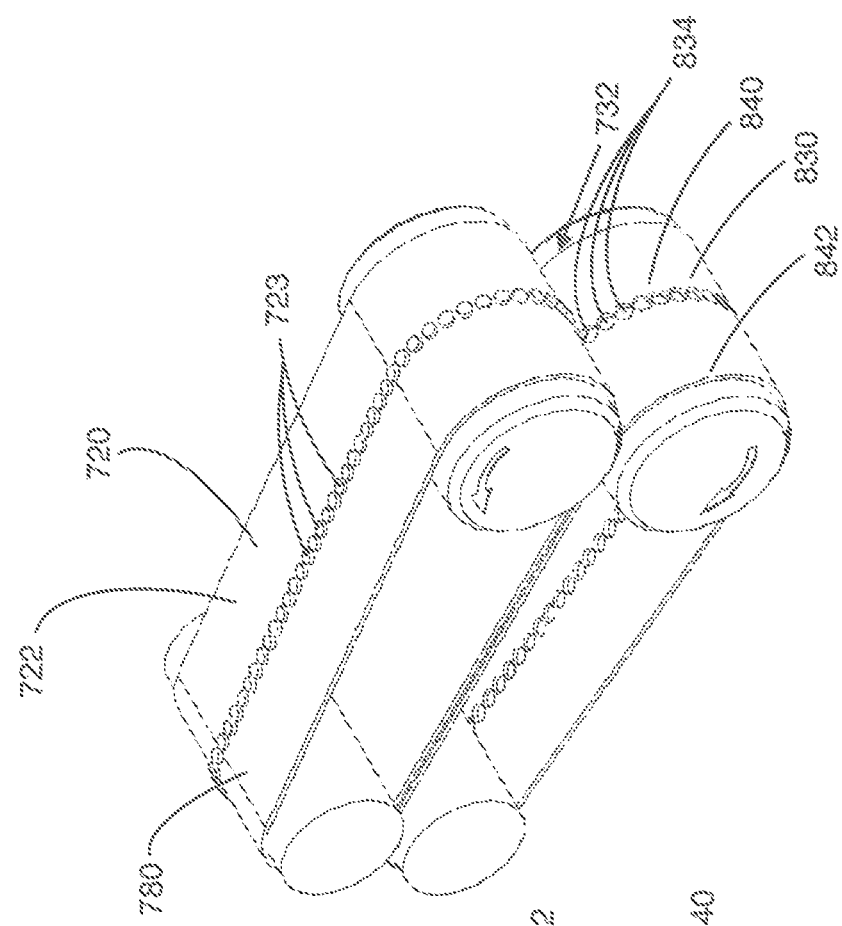
Figure 18:
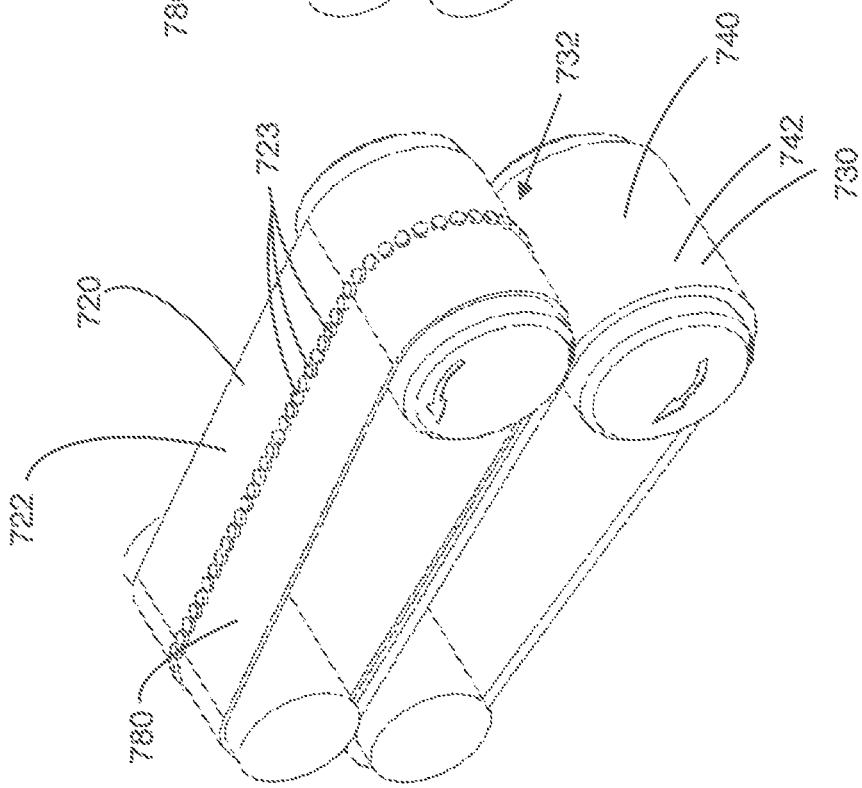

In yet other exemplary configurations, the press member 780 may be in the form of a first conveyor 720 as shown in FIG. 18. The first conveyor 720 may have an outer surface 722 and a plurality of projections 723 extending outward from the outer surface 722 of the first conveyor 720. An anvil roll 730 may be configured as a second conveyor 740 may be located adjacent to the first conveyor 720, forming a nip 732 there between. The second conveyor 740 may have an outer surface 742. The second conveyor 740 may comprise a compliant material. In other exemplary configurations, a second conveyor 840 may have a plurality of apertures 834 in an outer surface 842 such as shown in FIG. 19. The apertures 736 of the second conveyor 840 may be configured to mate with the projections 723 of the first conveyor 720. In some exemplary configurations, the second conveyor 840 shown in FIG. 19 may be made of a rigid material, such as metal.

It is to be appreciated that the methods and apparatuses disclosed herein may be used with various seaming apparatuses. For example, the methods and apparatuses disclosed herein may be used with U.S. patent application Ser. No. 13/401,907, filed Feb. 22, 2012 and U.S. patent application Ser. No. 13/402,056, filed Feb. 22, 2012.

Although the bonder apparatus is described in the context of bonding belts to make side seams, it is to be appreciated that the methods and apparatuses herein can be used to bond various components and substrates together. The apparatuses and methods for bonding substrates disclosed herein can also be configured to operate in accordance with the apparatus and methods disclosed in U.S. Pat. No. 6,248,195 and U.S. Patent Application Publication No. 2012-0021186, filed Jun. 7, 2010.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for forming a seam, the method comprising the steps of:
    rotating a drum about an axis of rotation, the drum comprising a fluid nozzle and a press member, the press member having an outer surface;
    rotating an anvil roll about an axis of rotation adjacent to the drum, the anvil roll having a compliant outer circumferential surface, the anvil roll and the drum forming a nip there between;
    advancing a first substrate layer in a machine direction onto the drum, the first substrate layer having an inner surface and an outer surface, wherein the outer surface of the first substrate layer is adjacent the drum;
    advancing a second substrate layer in the machine direction, the second substrate layer having an inner surface and an outer surface, wherein the first substrate layer is between the second substrate layer and the drum, wherein the first and second substrate layers have a combined, uncompressed caliper;
    wrapping the first and second substrate layers around a portion of the drum;
    heating a fluid to a temperature sufficient to at least partially melt the first and second substrate layers;
    moving the fluid nozzle radially outward relative to the axis of rotation of the drum;
    directing a jet of the heated fluid onto the first and second substrate layers;
    partially melting the first and second substrate layers;
    retracting the fluid nozzle radially inward relative to the axis of rotation of the drum;
    shifting the press member radially outward relative to the axis of rotation of the drum;
    advancing the first and second substrate layers through the nip; and
    compressing the first and second substrate layers between the press member and the anvil roll and deforming the compliant outer circumferential surface of the anvil roll.

2. The method of claim 1, wherein the anvil roll deforms by a radial thickness that is at least about 25% of the combined uncompressed caliper of the first and second substrate layers.

3. The method of claim 1, wherein the anvil roll deforms by a radial thickness that is at least about 50% of the combined uncompressed caliper of the first and second substrate layers.

4. The method of claim 3, wherein the anvil roll comprises a sleeve, wherein the sleeve forms the outer circumferential surface of the anvil roll.

5. The method of claim 1, wherein the compliant outer circumferential surface of the anvil roll has a shore A durometer of about 20 to about 100.

6. The method of claim 1, wherein the drum comprises an outer circumferential surface and a drum aperture in the outer circumferential surface, and wherein the fluid nozzle and press member are located radially inward from the aperture in the outer circumferential surface.

7. The method of claim 1, wherein the press member compresses the first and second substrate layers between the anvil roll at a pressure of about $1 \times 10^5$ Newtons per square meter to about $1 \times 10^8$ Newtons per square meter.

8. The method of claim 1, wherein the press member comprises a plurality of projections, the projections having an outer surface, wherein the step of compressing the first and second substrate layers between the press member and the anvil roll comprises compressing the first and second substrate layers between the projections of the press member and the anvil roll.

9. The method of claim 8, wherein the outer surface of the projections is rounded.

10. The method of claim 8, wherein the projections are spaced apart from each other projection.

11. The method of claim 1, further comprising the steps of:
    retracting the press member radially inward into the drum;
    shifting the press member radially outward from the drum;
    rotating a second anvil roll adjacent the drum, the second anvil roll comprising a compliant outer circumferential surface; and
    compressing the first and second substrate layers between the press member and the second anvil roll such that the press member deforms the compressible material of the anvil roll.

12. The method of claim 1, wherein the first and second substrate layers are nonwovens.

13. The method of claim 1, wherein the fluid is ambient air.

14. The method of claim 1, further comprising the step of cutting the first and second substrate layers into individual articles with a knife roll.

15. A method for forming a seam, the method comprising the steps of:
    rotating a drum about an axis of rotation, the drum comprising a fluid nozzle and a press member, the press member having an outer surface;
    rotating an anvil roll about an axis of rotation adjacent to the drum, the anvil roll having a compliant outer circumferential surface, the anvil roll and the drum forming a nip there between;
    advancing a first substrate layer in a machine direction onto the drum, the first substrate layer having an inner surface and an outer surface, wherein the outer surface of the first substrate layer is adjacent the drum;
    advancing a second substrate layer in the machine direction, the second substrate layer having an inner surface and an outer surface, wherein the first substrate layer is between the second substrate layer and the drum, wherein the first and second substrate layers have a combined, uncompressed caliper;
    wrapping the first and second substrate layers around a portion of the drum;
    heating a fluid to a temperature sufficient to at least partially melt the first and second substrate layers;
    moving the fluid nozzle radially outward relative to the axis of rotation of the drum;
    directing a jet of the heated fluid onto the first and second substrate layers;
    partially melting the first and second substrate layers;
    retracting the fluid nozzle radially inward relative to the axis of rotation of the drum;
    shifting the press member radially outward relative to the axis of rotation of the drum, wherein the press member comprises a plurality of projections;
    advancing the first and second substrate layers through the nip; and
    compressing the first and second substrate layers between the press member and the anvil roll and deforming the compliant outer circumferential surface of the anvil roll.

16. The method of claim 15, wherein the step of compressing the first and second substrate layers between the press member and the anvil roll comprises compressing the first and second substrate layers between the projections of the press member and the anvil roll.

17. The method of claim 15, wherein the anvil roll deforms by a radial thickness that is at least about 25% of the combined uncompressed caliper of the first and second substrate layers.

18. The method of claim 15, wherein the press member compresses the first and second substrate layers between the anvil roll at a pressure of about $1 \times 10^5$ Newtons per square meter to about $1 \times 10^8$ Newtons per square meter.

19. A method for forming a seam, the method comprising the steps of:
- rotating a drum about an axis of rotation, the drum comprising a fluid nozzle and a press member, the press member having an outer surface;
- rotating an anvil roll about an axis of rotation adjacent to the drum, the anvil roll having a compliant outer circumferential surface, the anvil roll and the drum forming a nip there between;
- advancing a first substrate layer in a machine direction onto the drum, the first substrate layer having an inner surface and an outer surface, wherein the outer surface of the first substrate layer is adjacent the drum;
- advancing a second substrate layer in the machine direction, the second substrate layer having an inner surface and an outer surface, wherein the first substrate layer is between the second substrate layer and the drum, wherein the first and second substrate layers have a combined, uncompressed caliper;
- wrapping the first and second substrate layers around a portion of the drum;
- heating a fluid to a temperature sufficient to at least partially melt the first and second substrate layers;
- moving the fluid nozzle radially outward relative to the axis of rotation of the drum;
- directing a jet of the heated fluid onto the first and second substrate layers;
- partially melting the first and second substrate layers;
- retracting the fluid nozzle radially inward relative to the axis of rotation of the drum;
- shifting the press member radially outward relative to the axis of rotation of the drum;
- advancing the first and second substrate layers through the nip;
- compressing the first and second substrate layers between the press member and the anvil roll and deforming the compliant outer circumferential surface of the anvil roll; and
- cutting the first and second substrate layers into individual articles.

20. The method of claim 19, wherein the first and second substrate layers are nonwovens.

* * * * *